(12) United States Patent
Noguchi et al.

(10) Patent No.: US 9,377,478 B2
(45) Date of Patent: Jun. 28, 2016

(54) SAMPLE-TEST-DEVICE MANAGEMENT SERVER, SAMPLE TEST DEVICE, SAMPLE TEST SYSTEM, AND SAMPLE TEST METHOD

(75) Inventors: Takashi Noguchi, Machida (JP); Yoshiyuki Tajima, Fujisawa (JP); Koji Kamoshida, Hitachinaka (JP); Naomi Ishii, Mito (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 358 days.

(21) Appl. No.: 13/322,773

(22) PCT Filed: Apr. 28, 2010

(86) PCT No.: PCT/JP2010/057572
§ 371 (c)(1),
(2), (4) Date: Feb. 13, 2012

(87) PCT Pub. No.: WO2010/137441
PCT Pub. Date: Dec. 2, 2010

(65) Prior Publication Data
US 2012/0144009 A1 Jun. 7, 2012

(30) Foreign Application Priority Data
May 27, 2009 (JP) .................................. 2009-127182

(51) Int. Cl.
G06F 15/173 (2006.01)
G01N 35/02 (2006.01)
G01N 35/00 (2006.01)

(52) U.S. Cl.
CPC ................ *G01N 35/02* (2013.01); *G01N 35/00* (2013.01); *G01N 35/0092* (2013.01); *G01N 35/0095* (2013.01); *G01N 35/00732* (2013.01)

(58) Field of Classification Search
CPC ............................. G01N 35/02; G01N 35/00
USPC ...................................... 709/223–224; 435/4
See application file for complete search history.

(56) References Cited

U.S. PATENT DOCUMENTS 5,988,857 A 11/1999 Ozawa et al.
2007/0254277 A1* 11/2007 Scrabeck et al. .................. 435/4

(Continued)

FOREIGN PATENT DOCUMENTS

JP 02-130678 5/1990
JP 10-062426 A 3/1998

(Continued)

OTHER PUBLICATIONS
International Search Report from PCT/JP010/057572, mailed Aug. 10, 2010.

*Primary Examiner* — Chris Parry
*Assistant Examiner* — Weiwei Stiltner
(74) *Attorney, Agent, or Firm* — Volpe and Koenig, P.C.

(57) ABSTRACT

There is provided a sample test system which can execute a prior process for a specific sample in consideration of priorities and process progresses of a plurality of samples processed in the sample test system. The sample test system includes a sample-test-device management server 101, when a specific-sample prior process request containing a specific sample ID and a prior-process-request level identification code is accepted from a sample access system 108, which selects a specific-sample prior-process-policy determination table based on the prior-process-request level identification code attached to the specific-sample prior process request, which determines a specific-sample prior process policy based on the specific-sample prior-process-policy determination table and a process state of the sample, which specifies a sample ID regarding the specific sample ID, and which transmits the specific-sample prior process policy to a sample-test-device group 119.

8 Claims, 24 Drawing Sheets

(56) References Cited

U.S. PATENT DOCUMENTS

| | | | |
|---|---|---|---|
| 2008/0020469 A1* | 1/2008 | Barnes et al. | 436/46 |
| 2009/0048870 A1* | 2/2009 | Godshall et al. | 705/3 |
| 2009/0143995 A1* | 6/2009 | Dinauer | G06F 19/28 702/19 |
| 2009/0275038 A1* | 11/2009 | Hodge | G06Q 10/0637 435/6.11 |
| 2010/0250174 A1 | 9/2010 | Tokunaga et al. | |

FOREIGN PATENT DOCUMENTS

| | | |
|---|---|---|
| JP | 11-281652 A | 10/1999 |
| JP | 3441960 B2 * | 9/2003 |
| JP | 2010-236962 A | 10/2010 |

* cited by examiner

FIG. 6A

DATA STRUCTURE OF SAMPLE REGISTRATION TABLE

| SAMPLE ID | CHILD SAMPLE ID | PRIORITY | PREDETERMINED END TIME |
|---|---|---|---|
| ⋮ | ⋮ | ⋮ | ⋮ |

FIG. 6B

DATA STRUCTURE OF SAMPLE-DEPENDENT PROCESS STATE MANAGEMENT TABLE

| SAMPLE ID | CHILD SAMPLE ID | START TIME | COMPLETION FLAG |
|---|---|---|---|
| ⋮ | ⋮ | ⋮ | ⋮ |

FIG. 6C

DATA STRUCTURE OF PRIORITY-DEPENDENT PROCESS STATE MANAGEMENT TABLE

| PRIORITY 1 | PRIORITY 2 | PRIORITY 3 | PRIORITY 4 | PRIORITY 5 | PRIORITY 6 |
|---|---|---|---|---|---|
| ⋮ | ⋮ | ⋮ | ⋮ | ⋮ | ⋮ |

FIG. 7

| PATIENT ID | SAMPLE ID | PRIORITY | PREDETERMINED END TIME | SAMPLE ITEM ID |
|---|---|---|---|---|
| ⋮ | ⋮ | ⋮ | ⋮ | ⋮ |

FIG. 8A

DATA STRUCTURE OF REQUEST-LEVEL/DETERMINATION-TABLE
CORRESPONDENCE TABLE

508 → 802, 801

| PRIOR PROCESS REQUEST LEVEL IDENTIFICATION CODE | PRIOR-PROCESS-POLICY DETERMINATION TABLE IDENTIFICATION CODE |
|---|---|
| ⋮ | ⋮ |

FIG. 8B

DATA STRUCTURE OF STORAGE TABLE OF
PRIOR-PROCESS-POLICY DETERMINATION TABLE 509, 806, 805, 804, 803

| DETERMINATION TABLE IDENTIFICATION CODE | NONE | | | | | | NO DELAY | | | | | | DELAY | | | | | |
|---|---|---|---|---|---|---|---|---|---|---|---|---|---|---|---|---|---|---|
| | 1 | 2 | 3 | 4 | 5 | 6 | 1 | 2 | 3 | 4 | 5 | 6 | 1 | 2 | 3 | 4 | 5 | 6 |
| ⋮ | ⋮ | ⋮ | ⋮ | ⋮ | ⋮ | ⋮ | ⋮ | ⋮ | ⋮ | ⋮ | ⋮ | ⋮ | ⋮ | ⋮ | ⋮ | ⋮ | ⋮ | ⋮ |

DOCTOR/AS SOON AS POSSIBLE

DOCTOR/SOON

OTHER-DEPARTMENT SERVER/AS SOON AS POSSIBLE

MESSAGE STRUCTURE OF SPECIFIC-SAMPLE PRIOR PROCESS REQUEST

MESSAGE STRUCTURE OF RESULT

MESSAGE STRUCTURE OF MEDIATION REQUEST

MESSAGE STRUCTURE OF PRIOR-PROCESS-POLICY SUPPLEMENT

MESSAGE STRUCTURE OF PROCESS PROGRESS

MESSAGE STRUCTURE OF PRIOR PROCESS POLICY

| 2501 | 2502 | 2503 | 2504 | 2505 | 2506 |
|---|---|---|---|---|---|
| PRIORITY1 | PRIORITY2 | PRIORITY3 | PRIORITY4 | PRIORITY5 | PRIORITY6 |
| ⋮ | ⋮ | ⋮ | ⋮ | ⋮ | ⋮ |

SAMPLE-TEST-DEVICE MANAGEMENT SERVER, SAMPLE TEST DEVICE, SAMPLE TEST SYSTEM, AND SAMPLE TEST METHOD

TECHNICAL FIELD

The present invention relates to a sample-test-device management server, sample test system, and a sample test method, and, more particularly, the present invention relates to processes performed when a preprocess device for a sample prior to a test and an analysis device for analyzing the sample on which the preprocess has been completed are used.

BACKGROUND ART

In recent years, by introducing a sample test system configured of a preprocess device, an analysis device, and others to a laboratory of a hospital, a test process can be speeded up, and a test result can be quickly reported to a doctor.

Also, for samples with different requirements in quickness such as a regular test for an inpatient, a test for an outpatient, and a test for an intraoperative patient, the test result can be reported in accordance with the requirements by allocating a priority to the samples in accordance with the requirements. For example, in the preprocess device, this is handled by preferentially feeding the sample to which a high priority is allocated. Further, Japanese Patent Application Laid-Open Publication No. H11-281652 describes a technique of handling this, if the preprocess for a specific sample is desired to be advanced, by updating the priority of the sample which has been previously allocated in the preprocess device.

PRIOR ART DOCUMENT

Patent Document

Patent Document 1: Japanese Patent Application Laid-Open Publication No. H11-281652

DISCLOSURE OF THE INVENTION

Problems to be Solved by the Invention

However, in Patent Document 1, the priority cannot be updated in a sample test system in consideration of the priority of the sample to be parallely processed with the update of the priority and process progress thereof. Therefore, when the priority of the specific sample is updated, there is a problem that the process for the sample to be parallely processed with the specific sample is unnecessarily delayed.

Also, it is difficult to provide a mechanism of updating the priority allocated to the specific sample to a doctor in order to reduce the above-described problem. Therefore, when a request of the update for the specific sample exists, it is required that this is handled by an inquiry from the doctor to an operator by phone, which can become one of main factors in decreasing operation efficiency of the operator.

Accordingly, a preferred aim of the present invention is to provide a sample-test-device management server, sample test system, and sample test method capable of performing prior process for a specific sample in consideration of a priority of a sample and process progress thereof.

The above and other preferred aims and novel characteristics of the present invention will be apparent from the description of the present specification and the accompanying drawings.

Means for Solving the Problems

A summary of the typical one of the inventions disclosed in the present application will be briefly described as follows.

That is, in the summary of the typical one, a processing unit is provided, in which, when a specific-sample prior process request containing a specific sample ID and a prior-process-request level identification code is received from a sample access system, the processing unit selects a specific-sample prior-process-policy determination table based on the prior-process-request level identification code attached to the specific-sample prior process request, determines a specific-sample prior process policy based on the specific-sample prior-process-policy determination table and a process state of the sample, specifies a sample ID for the specific sample ID, and transmits the specific-sample prior process policy to a sample-test-device group.

Effects of the Invention

The effect obtained by typical aspects of the present invention will be briefly described below.

That is, as the effect obtained by the typical aspects of the present invention, a prior process can be preformed for a specific sample in consideration of a priority of a sample and process progress thereof.

BRIEF DESCRIPTIONS OF THE DRAWINGS

FIGS. 6A to 6C are diagrams each showing a data structure example of a data stored in a test management memory of the sample-test-device management server of the sample test system for performing the sample test method according to the embodiment of the present invention;

FIG. 7 is a diagram showing a structure example of a sample registration table owned by a clinical-test-department server of the sample test system for performing the sample test method according to the embodiment of the present invention;

FIGS. 8A and 8B are diagrams each showing a data structure of a data stored in a policy management DB of the sample-test-device management server of the sample test system for performing the sample test method according to the embodiment of the present invention;

Figures 24, 25:
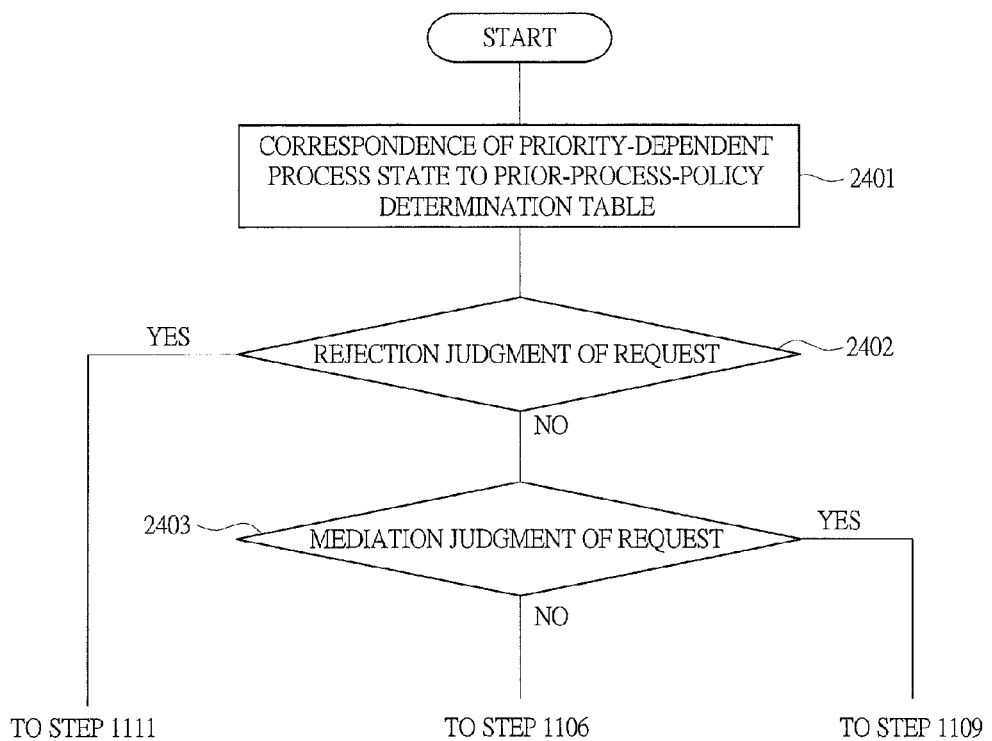
FIG. 24 is a diagram showing a process flow of a prior-process-policy management unit at a step 1105 shown in FIG. 11.
Figure 26:
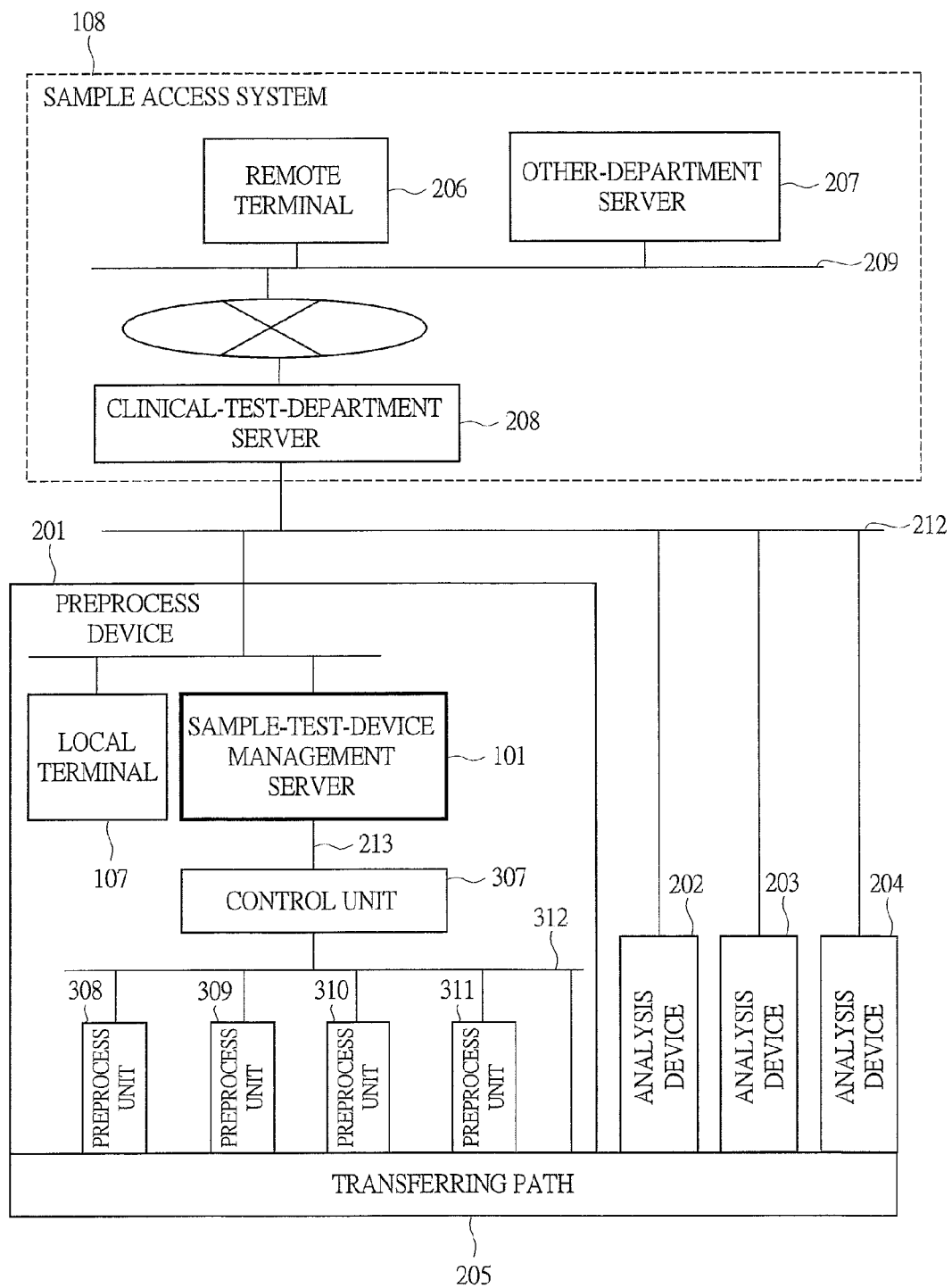

FIG. 25 is a diagram showing a data structure of a protective condition storage table contained in each test management memory of the sample test system for performing the sample test method according to the embodiment of the present invention; and FIG. 26 is a configuration example in which a sample-test-device management server 101 and a local terminal 107 are embedded in a preprocess device 201.

BEST MODE FOR CARRYING OUT THE INVENTION

Hereinafter, an embodiment of the present invention will be described in detail with reference to the accompanying drawings. Note that the same components are denoted by the same reference symbols throughout the drawings for describing the embodiment, and the repetitive description thereof will be omitted.

In the description of the present invention below, the description is made for a sample test method in which, in a state that a sample test system is during executing tests for a plurality of samples, a prior process request for specifying a sample which is specified (hereinafter referred to as a specific sample) from the plurality of samples is accepted, and the request is executed in consideration of a plurality of process states.

More particularly, in the present embodiment, the description is made on an assumption that a priority is allocated to each of the plurality of samples, that a test is executed based on the priority in the sample test system, and that a request is accepted from a clinic or a roentgen test department via a network.

Figure 1:
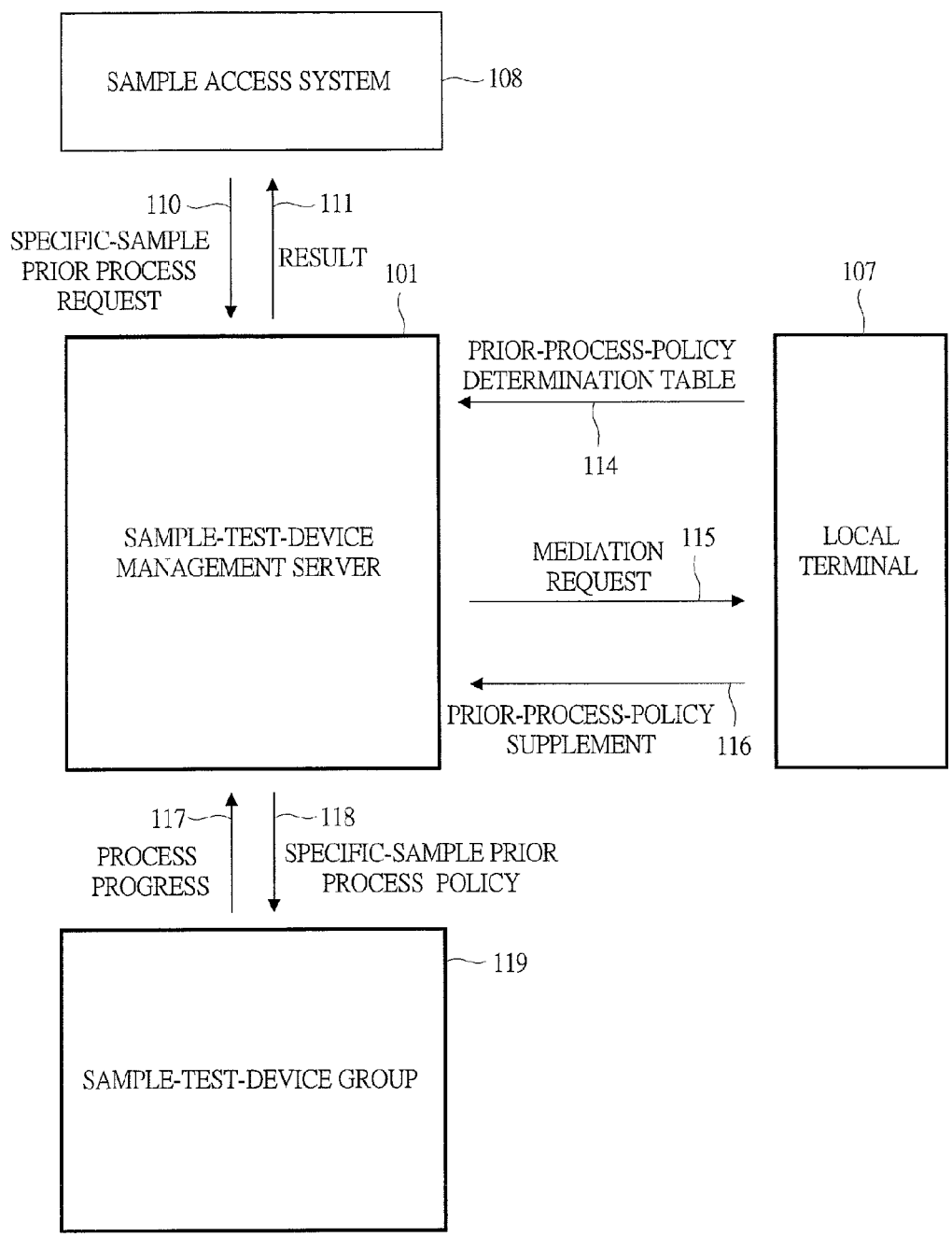
FIG. 1 is a diagram showing components of a sample test system and a message flow thereof for performing a sample test method according to an embodiment of the present invention.

FIG. 1 is a diagram showing components of a sample test system and a message flow thereof for performing a sample test method according to an embodiment of the present invention.

In FIG. 1, the sample test system is configured of: a sample-test-device group 119; a sample-test-device management server 101; a local terminal 107; and a sample access system 108.

The sample-test-device management server 101 and the sample access system 108 transmit and receive a specific-sample prior process request 110 which is a prior process request for a specific sample and a result 111 which is a result of the specific-sample prior process request 110 in a message format.

Also, the sample-test-device group 119 and the sample-test-device management server 101 transmit and receive a process progress 117 which is a process progress of a sample and a specific-sample prior process policy 118 which is a policy of a prior process for the specific sample in a message format.

Further, the sample-test-device management server 101 and the local terminal 107 transmit and receive a prior-process-policy determination table 114 for determining a policy of a prior process for the specific-sample prior process request 110 and the process progress 117, a mediation request 115 for requesting an operator for the mediation, and a prior-process-policy supplement 116 which is a supplement of the prior process policy in a message format.

Figure 2:
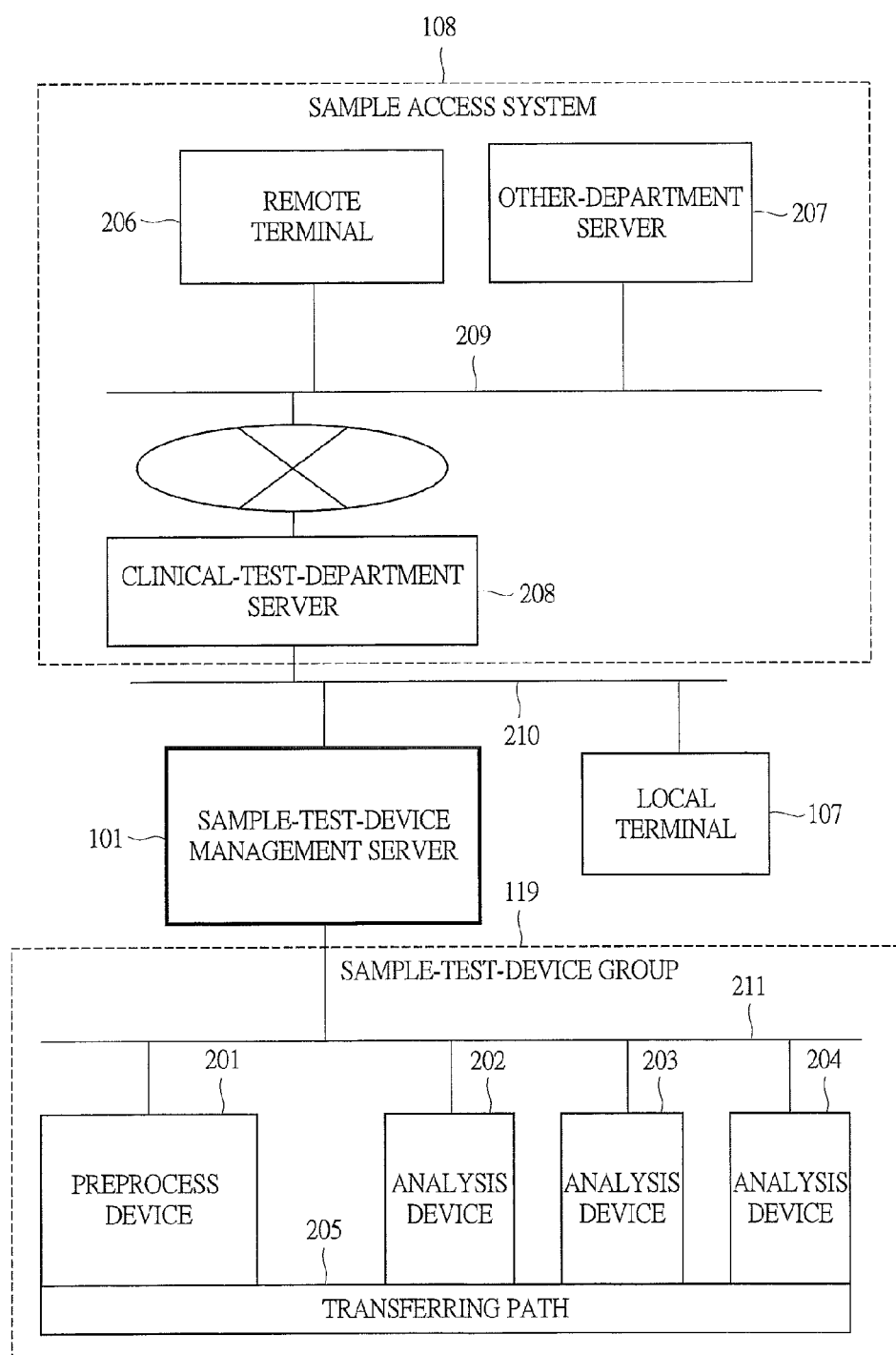
FIG. 2 is a diagram showing a network configuration of the sample test system for performing the sample test method according to the embodiment of the present invention.

FIG. 2 is a diagram showing a network configuration of the sample test system for performing the sample test method according to the embodiment of the present invention.

In FIG. 2, in the sample test system, the sample-test-device group 119, the sample-test-device management server 101, the local terminal 107, and the sample access system 108 are coupled with each other via a network. Also, in the sample access system 108, a remote terminal 206 for making a request for registering a sample test and others, a clinical-test-department server 208 for managing a registration and a result of a clinical test and others, and an other-department server 207 which is a server of a roentgen-test department are coupled with each other via a network 209.

Also, the sample-test-device group 119 is configured of: a preprocess device 201 for stocking a sample stored in a test tube, opening operation a cap of the test tube, dispensing the sample so as to divide it into a plurality of child samples, and others; a transferring path 205 for capturing, feeding, and transferring the sample; and analysis devices (202, 203, and 204) for analyzing the child samples, which are coupled with each other via a network 211.

The clinical-test-department server 208, the sample-test-device management server 101, and the local terminal 107 are coupled with each other via a network 210. Also, the sample-test-device management server 101, the preprocess device 201, and the analysis devices (202, 203, and 204) are coupled with each other via the network 211.

In the present embodiment, it is assumed that a doctor in a consulting room makes a prior process request for a specific sample from the remote terminal 206. Also, it is assumed that a laboratory technician in the roentgen department makes a prior process request for a specific sample from a terminal coupled with the other-department server 207 although not shown. Further, it is assumed that a program stored in the other-department server 207 makes a prior process request for a specific sample. Note that the prior process request may be made by cooperation of the remote terminal 206 and the other-department server 207.

Figure 5:
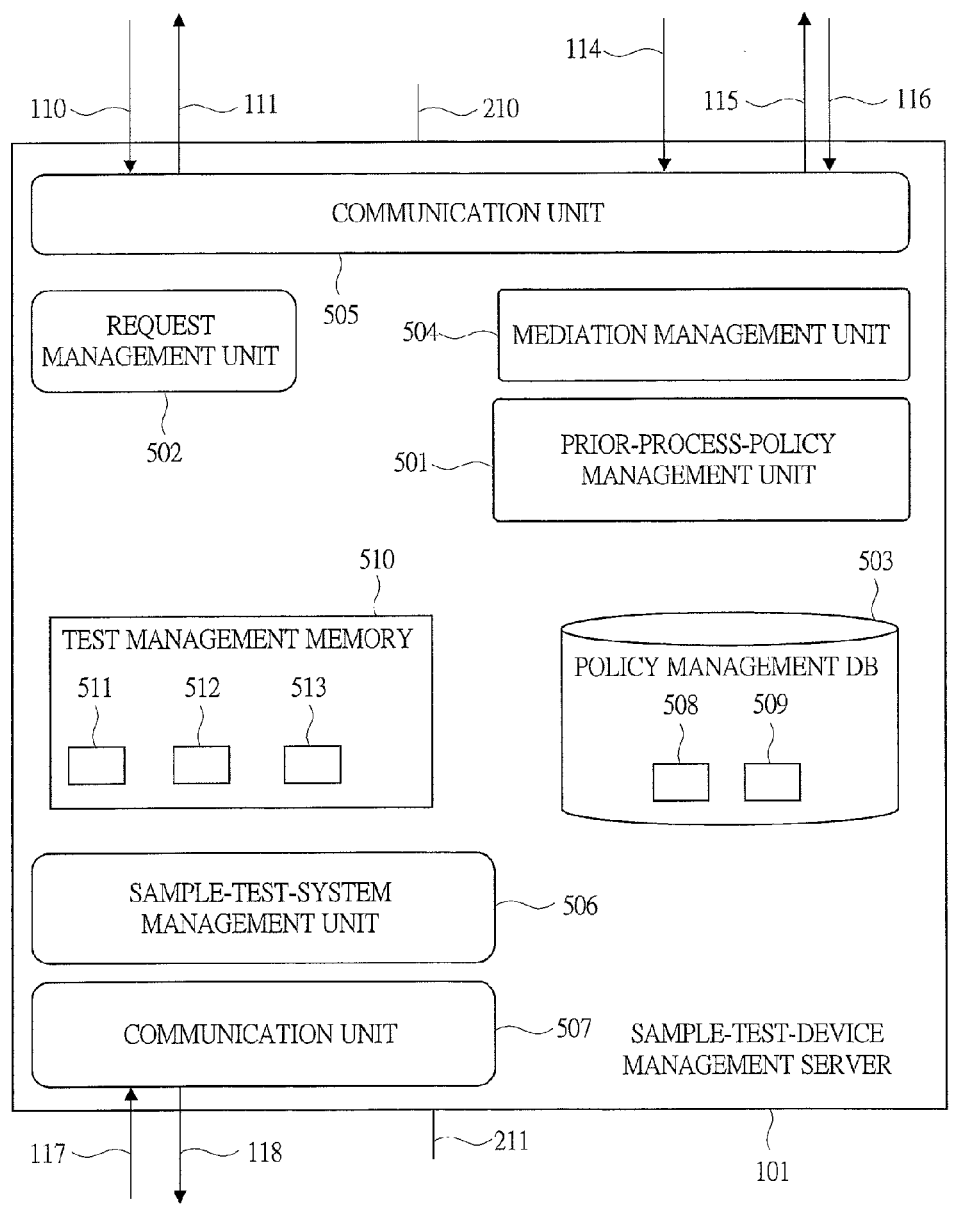
FIG. 5 is a diagram showing a software configuration of a sample-test-device management server of the sample test system for performing the sample test method according to the embodiment of the present invention.

FIG. 5 is a diagram showing a software configuration of the sample-test-device management server of the sample test system for performing the sample test method according to the embodiment of the present invention.

In FIG. 5, the sample-test-device management server 101 is configured of: a communication unit 505 for performing communication via the network 210; a request management unit 502 for managing a request for the specific sample; a prior-process-policy management unit 501 for managing a prior process policy for the specific sample; a mediation management unit 504 for managing mediation by the operator; a sample-test-system management unit 506 for managing a process state of a sample test and others; a communication unit 507 for performing communication via the network 211; a policy management DB 503 for storing a request-level/determination-table correspondence table 508 and a prior-process-policy determination table storage table 509; and a test management memory 510 for storing a sample registration table 511, a sample-dependent process state management table 512, and a priority-dependent process state management table 513.

Figure 14:
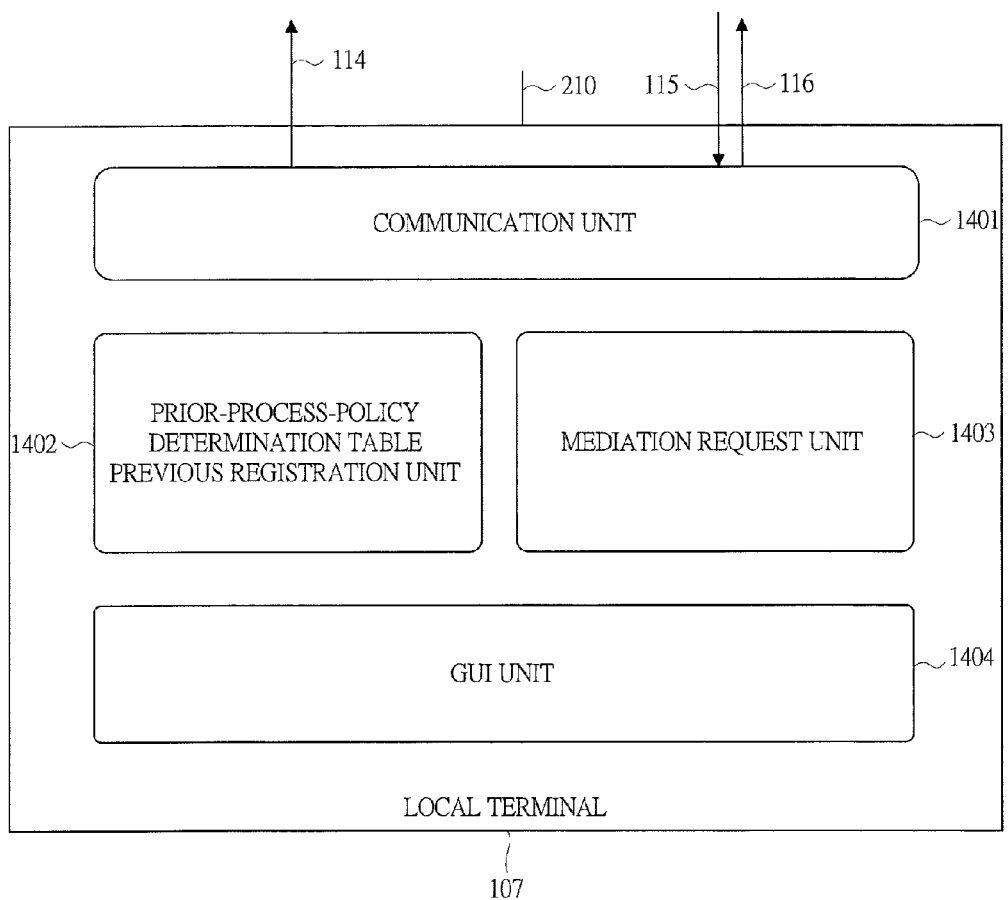
FIG. 14 is a diagram showing a software configuration of a local terminal of the sample test system for performing the sample test method according to the embodiment of the present invention.

FIG. 14 is a diagram showing a software configuration of the local terminal of the sample test system for performing the sample test method according to the embodiment of the present invention.

In FIG. 14, the local terminal 107 is configured of: a communication unit 1401 for performing communication via the network 210; a prior-process-policy determination table previous registration unit 1402 for previously registering the prior-process-policy determination table; a mediation request unit 1403 for making a request for mediation in determination of the prior process policy, and a GUI unit 1404.

Figure 3:
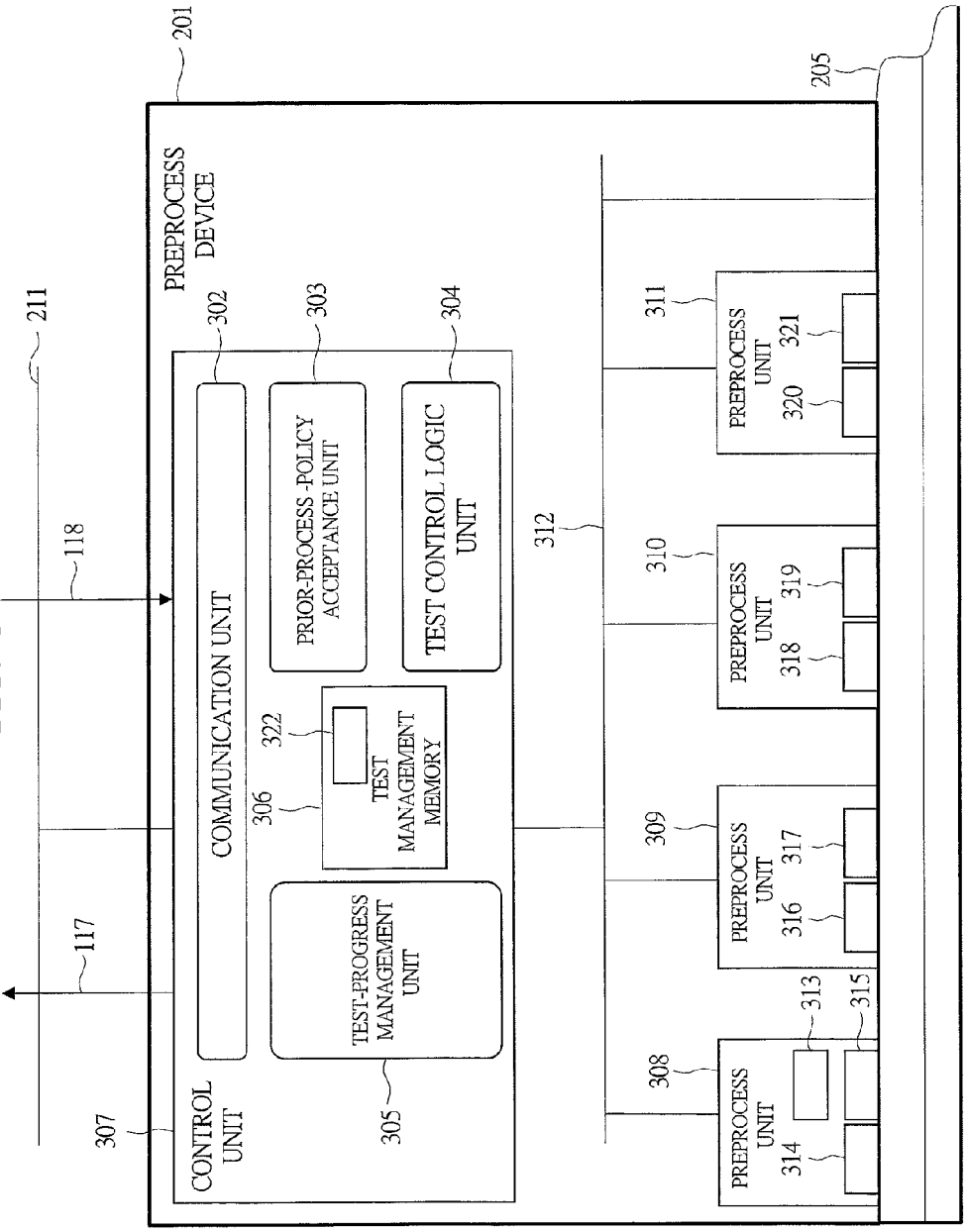
FIG. 3 is a diagram showing a preprocess device configuration of the sample test system for performing the sample test method according to the embodiment of the present invention.

FIG. 3 is a diagram showing a preprocess device configuration of the sample test system for performing the sample test method according to the embodiment of the present invention.

In FIG. 3, the preprocess device 201 is configured of: a control unit 307; and preprocess units (308, 309, 310, and 311). Also, the control unit 307 is configured of: a communication unit 302 for performing communication via the network 211; a test progress management unit 305 for managing the progress of the sample test; a prior-process-policy acceptance unit 303 for accepting a policy of priority control; a test control logic unit 304 for controlling the preprocess units (308, 309, 310, and 311) and the transferring path 205; and a test management memory 306 in which a protective condition storage table 322 and others is contained.

The preprocess units (308, 309, 310, and 311) are configured of: respective feeding units (314, 316, 318, and 320) for feeding a sample which is a process target to the transferring path 205; and respective capturing units (315, 317, 319, and 321) for capturing a sample from the transferring path 205.

Here, the preprocess unit 308 is a stocker for orderly storing samples. Therefore, the preprocess unit 308 includes an arm 313 having a function for arranging a sample to be fed of the orderly-arranged samples to the feeding unit 314 and a function of orderly arranging the samples at the capturing unit 315.

The test control logic unit 304 of the preprocess device 201 controls the preprocess units (308, 309, 310, and 311) and the transferring path 205 based on a sample ID, a priority, and a test item ID to perform preprocess such as the dispensing and the transferring for the sample.

Also, the test progress management unit 305 collects a progress state of the preprocess from the preprocess units (308, 309, 310, and 311) and the transferring path 205 to store the state in the test management memory 306. Further, the test progress management unit 305 reads the progress state of the preprocess stored in the test management memory 306 at a predetermined timing, and then, transmits the state to the sample-test-device management server 101 via the communication unit 302 and the network 211.

Figure 13:
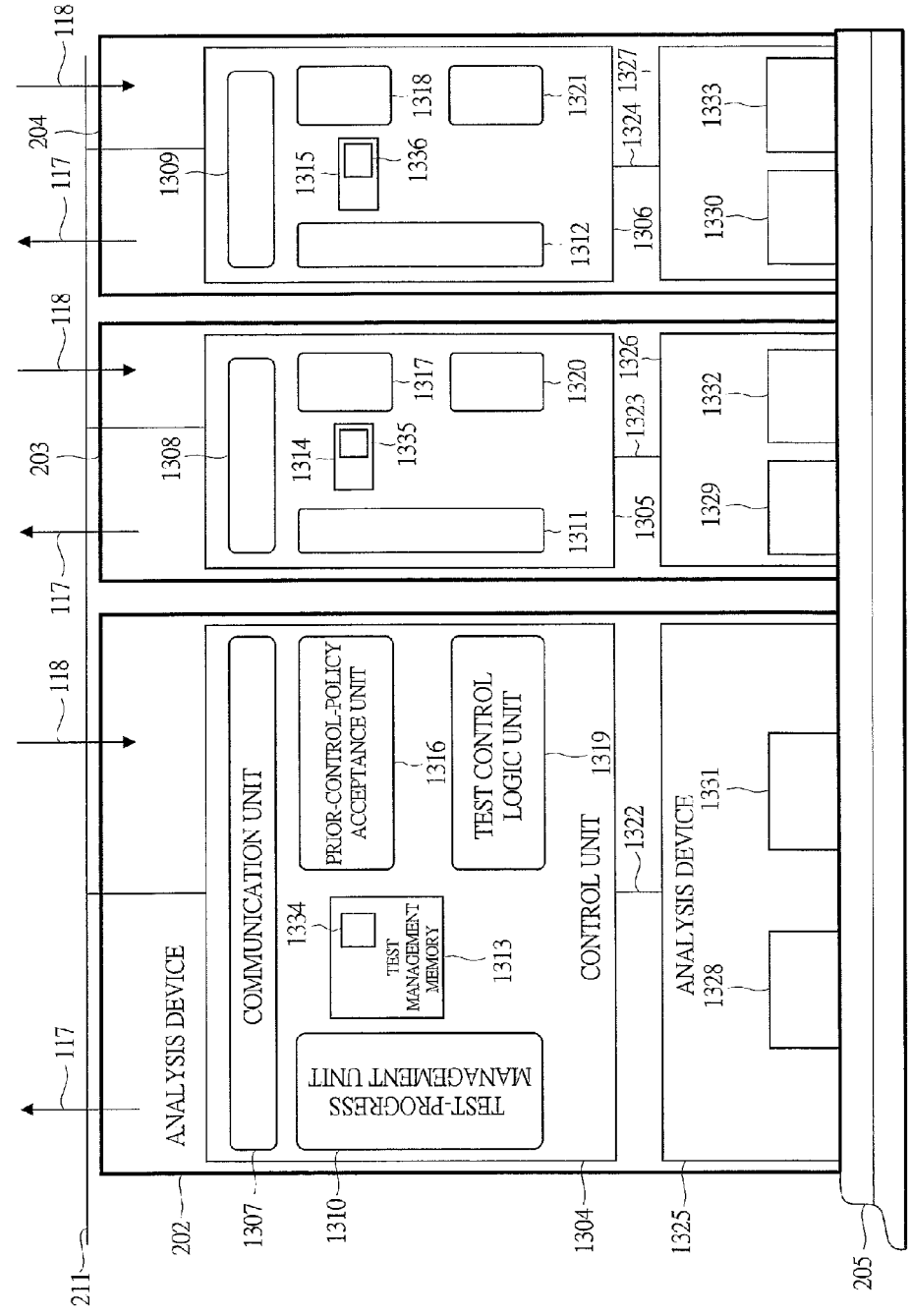
FIG. 13 is a diagram showing a configuration of an analysis device of THE sample test system for performing THE sample test method according to the embodiment of the present invention.

FIG. 13 is a diagram showing a configuration of an analysis device of the sample test system for performing the sample test method according to the embodiment of the present invention.

In FIG. 13, in the analysis devices (202, 203, and 204), respective control units (1304, 1305, and 1306) and respective analysis units (1325, 1326, and 1327) are coupled with each other via respective networks (1322, 1323, and 1324).

The control units (1304, 1305, and 1306) are configured of: respective communication units (1307, 1308, and 1309) for performing communication via the network 211; respective test progress management units (1310, 1311, and 1312) for managing the progress of the sample test; respective prior-process-policy acceptance units (1316, 1317, and 1318) for accepting the prior process policy; respective test control logic units (1319, 1320, and 1321) for controlling the respective analysis units (1325, 1326, and 1327); and respective test management memories (1313, 1314, and 1315) in which respective protective condition storage tables (1334, 1335, and 1336) and others are contained.

The analysis units (1325, 1326, and 1327) are configured of: respective feeding units (1328, 1329, and 1330) for feeding a sample which is a process target to the transferring path 205; and respective capturing units (1331, 1332, and 1333) for capturing a sample from the transferring path 205.

The test control logic units (1319, 1320, and 1321) of the respective analysis devices (202, 203, and 204) control the respective analysis devices (1325, 1326, and 1327) based on a sample ID, a child sample ID, a priority, and a test item ID which are transmitted from the sample-test-device management server 101, to analyze a child sample.

Also, the test progress management units (1310, 1311, and 1312) collect a state of the analysis progress from the respective analysis devices (1325, 1326, and 1327) to store the state in the respective test management memories (1313, 1314, and 1315).

Further, the test progress management units (1310, 1311, and 1312) read the state of the analysis progress stored in the respective test management memories (1313, 1314, and 1315) at a predetermined timing, and then, transmit the state to the sample-test-device management server 101 via the respective communication units (1307, 1308, and 1309) and the network 211.

FIG. 7 is a diagram showing a structure example of a sample registration table owned by the clinical-test-department server of the sample test system for performing the sample test method according to the embodiment of the present invention.

In FIG. 7, the sample registration table is configured of: a patient ID 701; a sample ID 702; a priority 703; a predetermined end time 704; and a test item ID 705. The sample registration table is transferred, for example, from the remote terminal 206 to the clinical-test-department server 208 via the network 209. The sample ID 702 is an ID allocated to a test target such as blood and urine. Any one of blood, urine, and others may be the test target, or a plurality of them may be the test target.

In the present embodiment, it is assumed that the predetermined end time 704 is determined based on a sample type such as an inpatient sample and an outpatient blood collection sample. For example, the above-described sample type can be judged from the patient ID 701. The sample type may be judged by a doctor or others or judged by a software program. Also, in order to determine the predetermined end time 704, the above-described judgment may be made in consideration of the test item ID 705 or others.

FIGS. 6A to 6C are diagrams each showing a data structure example of a data stored in the test management memory of the sample-test-device management server of the sample test system for performing the sample test method according to the embodiment of the present invention, FIG. 6A shows a sample registration table data structure which is a data structure of the sample registration table 511, FIG. 6B shows a sample-dependent process state management table data structure which is a data structure of the sample-dependent process state management table 512, and FIG. 6C shows a priority-dependent process state management table data structure which is a data structure of the priority-dependent process state management table 513.

First, the data structure of the sample registration table in FIG. 6A is configured of: a sample ID 601; a child sample ID 602; a priority 603; and a predetermined end time 604.

Next, the data structure of the sample-dependent process state management table in FIG. 6B is configured of: a sample ID 605; a child sample ID 606; a start time 607; and a completion flag 608.

Next, the data structure of the priority-dependent process state management table in FIG. 6C is configured of: a priority 1 (609); a priority 2 (610); a priority 3 (611); a priority 4 (612); a priority 5 (613); and a priority 6 (614).

Hereinafter, a procedure of creating the sample registration table 511 and the sample-dependent process state management table 512 stored in the sample management memory 510 is described as one example.

First, the clinical-test-department server 208 transmits the sample ID, the priority, the predetermined end time, and the test item ID, which are shown in the sample registration table in FIG. 7, to the sample-test-device management server 101 via the network 210.

The sample-test-device management server 101 receives the sample ID, the priority, the predetermined end time, and the test item ID, and stores the sample ID, the priority, and the predetermined end time, into the sample ID 601, the priority 603, and the predetermined end time 604 in the sample registration table 511, respectively.

Next, the sample-test-device management server 101 transmits the sample ID, the priority, and the test item ID, to the preprocess device 201 via the network 211. The preprocess device 201 performs the dispensing process which divides the sample into the child samples based on the sample ID, the priority, and the test item ID, and then, transmits a set of the sample ID and the child sample ID and the start time to the sample-test-device management server 101.

The sample-test-device management server 101 receives the set of the sample ID and the child sample ID and the start time, and then, first, stores the child sample ID into the child sample ID 602 in the sample registration table 511.

Next, it stores the sample ID, the child sample ID, and the start time into the sample ID 605, the child sample ID 606, and the start time 607 in the sample-dependent process state management table 512, respectively.

FIGS. 8A and 8B are diagrams each showing a data structure of a data stored in the policy management DB of the sample-test-device management server of the sample test system for performing the sample test method according to the embodiment of the present invention, FIG. 8A shows a request-level/determination-table correspondence table data structure which is a data structure of the request-level/determination-table correspondence table 508 stored in the policy management DB 503, and FIG. 8B shows a prior-process-policy determination table storage table data structure which is a data structure of the prior-process-policy determination table storage table 509.

First, the data structure of the request-level/determination-table correspondence table of FIG. 8A is configured of: a prior-process-request level identification code 802; and a prior-process-policy determination table identification code 801.

The data structure of the prior-process-policy determination table storage table in FIG. 8B is configured of: a determination table identification code 806; "NONE" 805; "NO DELAY" 804; and "DELAY" 803.

FIG. 25 is a diagram showing a data structure of a protective condition storage table contained in each test management memory of the sample test system for performing the sample test method according to the embodiment of the present invention.

In FIG. 25, in the respective protective condition storage tables (1334, 1335, 1336 and 322) included in the test management memories (1313, 1314, 1315, and 306), a protective flag is stored for each of priorities (2501, 2502, 2503, 2504, 2505, and 2506).

Figure 15A:
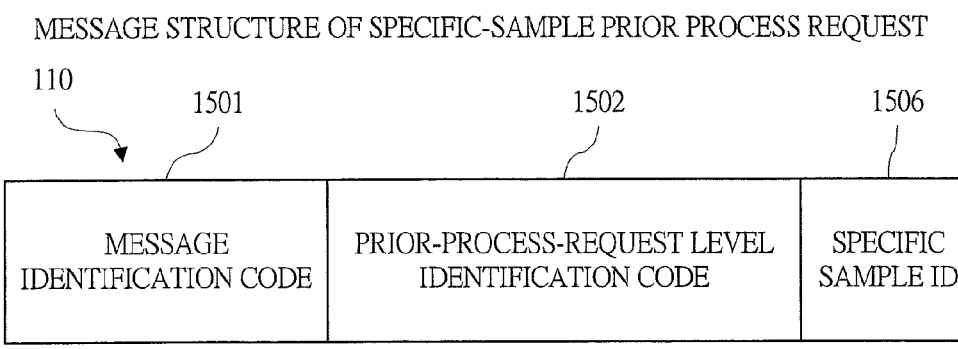
FIGS. 15A and 15B are diagrams each showing a message structure between a sample-test-device management server and a sample access system of the sample test system for performing the sample test method according to the embodiment of the present invention.
Figure 15B:
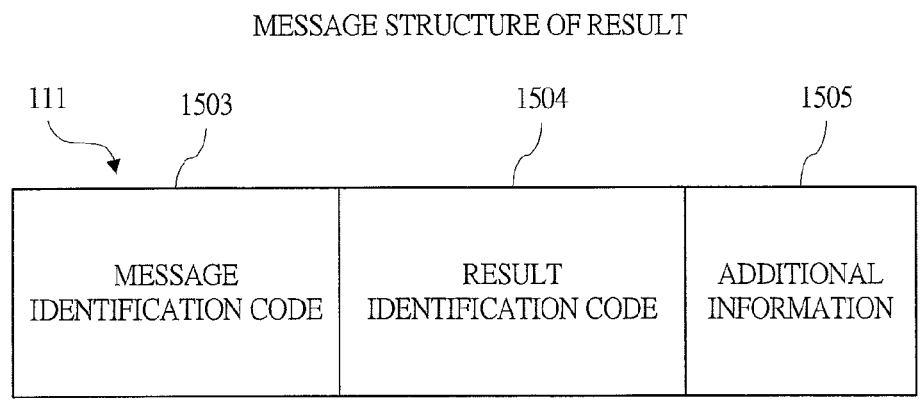

FIGS. 15A and 15B are diagrams each showing a message structure between the sample-test-device management server and the sample access system of the sample test system for performing the sample test method according to the embodiment of the present invention, FIG. 15A shows a specific-sample prior-process-request message structure which is a message structure of the specific-sample prior process request 110, and FIG. 15B shows a result message structure which is a message structure of the result 111.

The message structure of the specific-sample prior process request of FIG. 15A is configured of: a message identification code 1501; a prior-process-request level identification code 1502; and a specific-sample ID 1506.

In the present embodiment, the prior-process-request level identification code 1502 is configured of a requester's attribution and a request level. The requester is a clinic doctor who requests the prior process for the specific sample. Alternatively, the requester is a test staff in the roentgen department. Further, the requester is not necessarily a human, and may be the other-department server 207 installed in the roentgen department. The request level indicates a level of a request for the prior process assumed by the requester, and, more specifically, is specified by an index such as "as soon as possible" or "soon".

Next, the message structure of the result of FIG. 15B is configured of: a message identification code 1503; a result identification code 1504; and additional information 1505.

Figure 16A:
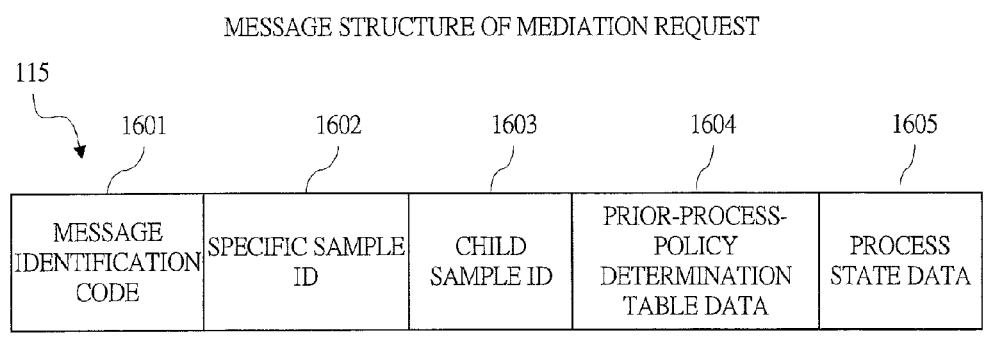
FIGS. 16A and 16B are diagrams each showing a message structure between a sample-test-device management server and a local terminal of the sample test system for performing the sample test method according to the embodiment of the present invention.
Figure 16B:
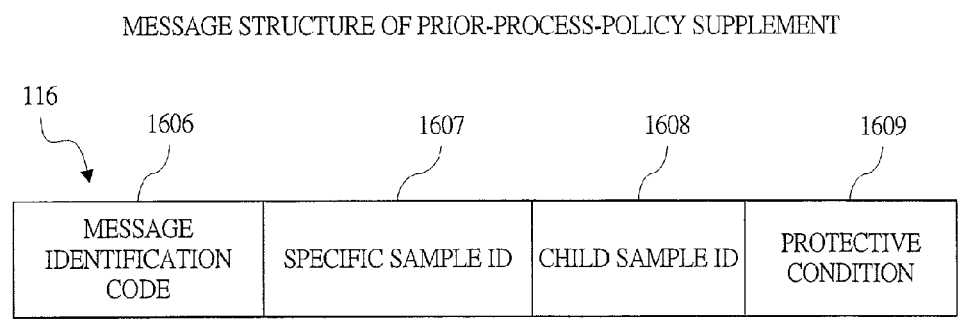

FIGS. 16A and 16B are diagrams each showing a message structure between the sample-test-device management server and the local terminal of the sample test system for performing the sample test method according to the embodiment of the present invention, FIG. 16A shows a mediation request message structure which is a message structure of the mediation request 115, and FIG. 16B shows a prior-process-policy supplement message structure which is a message structure of the prior-process-policy supplement 116.

First, the message structure of the mediation request of FIG. 16A is configured of: a message identification code 1601; a specific-sample ID 1602; a child sample ID 1603; a prior-process-policy determination table data 1604; and a process state data 1605.

Next, the message structure of the prior-process-policy supplement of FIG. 16B is configured of: a message identification code 1601; a specific-sample ID 1607; a child sample ID 1608; and a protective condition 1609.

Here, the protective condition 1609 indicates a protective condition for a sample test parallely processed with a process of the acceptance of the specific-sample prior process request 110 by the sample-test-device management server 101. The protective condition 1609 is specified with a set of the priority and the protective flag. If it is required to protect the sample, the number of 1 is specified as the protective flag.

On the other hand, if it is not required to protect the sample, the number of 0 is specified as the protective flag. For example, if it is required to protect a sample test with a priority of 2, the numbers of 2 and 1 are specified. Note that the protective condition may not be specified.

Figure 17A:
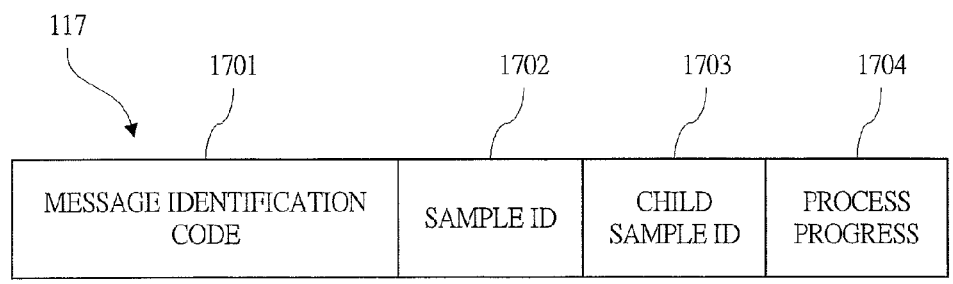
FIGS. 17A and 17B are diagrams each showing a message structure between a sample-test-device management server and a sample-test-device group of the sample test system for performing the sample test method according to the embodiment of the present invention.
Figure 17B:
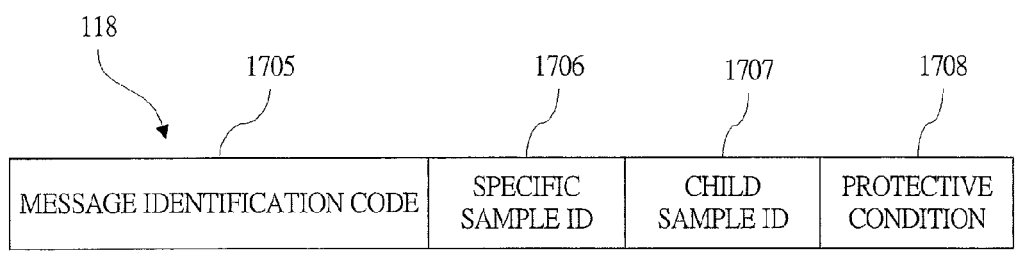

FIGS. 17A and 17B are diagrams each showing a message structure between the sample-test-device management server and the sample-test-device group of the sample test system for performing the sample test method according to the embodiment of the present invention, FIG. 17A shows a process progress message structure which is a message structure of the process progress 117, and FIG. 17B shows a prior-process-policy message structure which is a message structure of the specific-sample prior process policy 118.

First, the message structure of the process progress of FIG. 17A is configured of: a message identification code 1701; a sample ID 1702; a child sample ID 1703; and a process progress 1704.

Next, the message structure of the prior process policy of FIG. 17B is configured of: a message identification code 1705; a specific-sample ID 1706; a child sample ID 1707; and a protective condition 1708. Note that the protective condition 1708 is used synonymously with the protective condition 1609.

Figure 18:
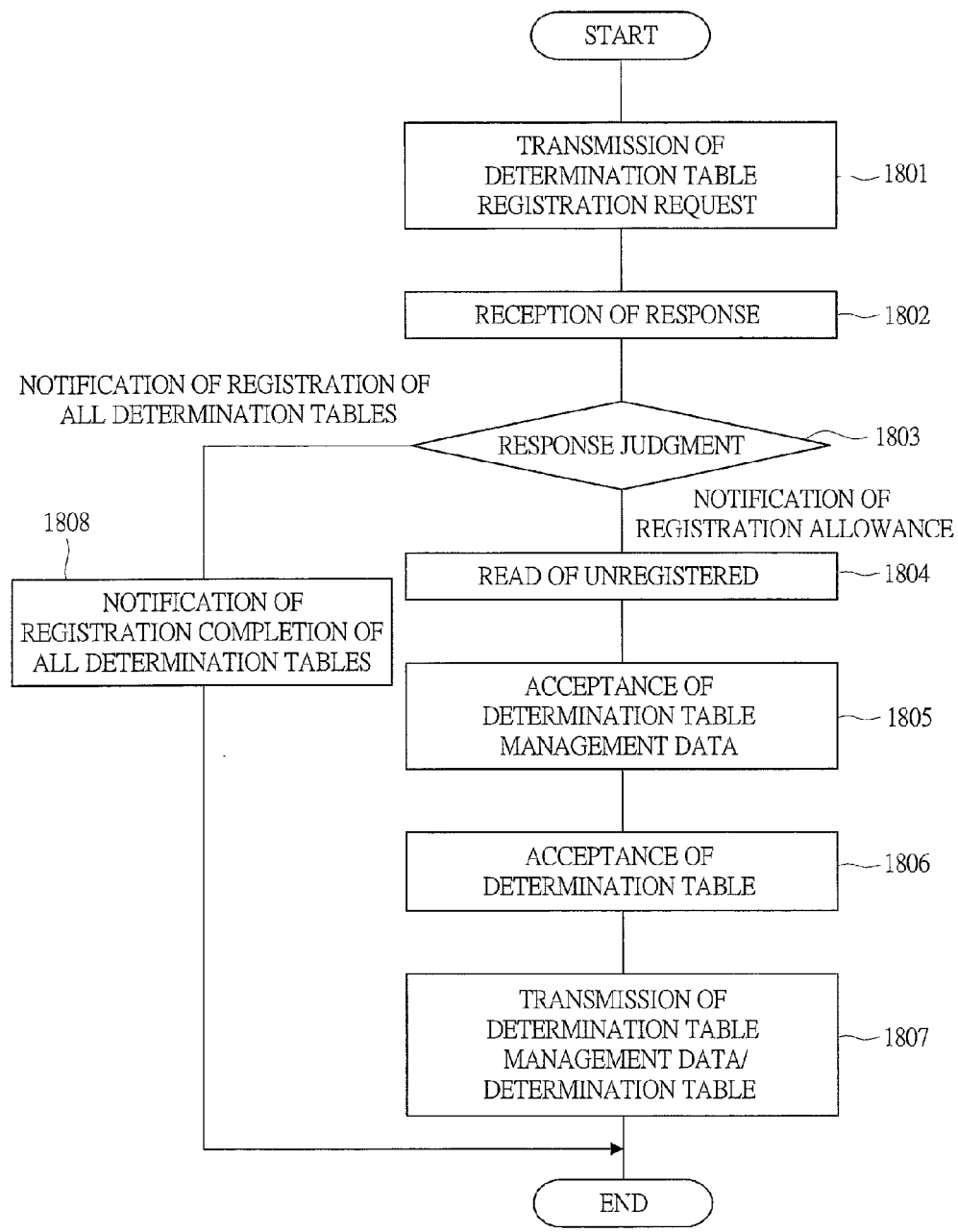
FIG. 18 is a diagram showing a process flow of a local terminal performed when an operator registers a specific-sample prior-process-policy determination table, in the sample test method according to the embodiment of the present invention.

FIG. 18 is a diagram showing a process flow of the local terminal performed when the operator registers the specific-sample prior-process-policy determination table in the sample test method according to the embodiment of the present invention.

First, the GUI unit 1404 accepts a registration request of the specific-sample prior-process-policy determination table from the operator, and then, notifies the prior-process-policy determination table previous registration unit 1402 of the registration request of the prior-process-policy determination table. The prior-process-policy determination table previous registration unit 1402 transmits the registration request of the prior-process-policy determination table, which is not shown in the drawing, to the sample-test-device management server 101 via the communication unit 1401 (at a step 1801).

Next, the prior-process-policy determination table previous registration unit 1402 receives a response, which is not shown in the drawing, from the sample-test-device management server 101 via the communication unit 1401 (at a step 1802).

Next, the prior-process-policy determination table previous registration unit 1402 judges the response (at a step 1803). If the prior-process-policy determination table previous registration unit 1402 judges at the step 1803 that the response is a notification of the registration allowance, all prior-process-request level identification codes attached to the response are read (at a step 1804).

Next, by the prior-process-policy determination table previous registration unit 1402, the prior-process-request level identification code is displayed on a screen via the GUI unit 1404, and the prior-process-policy determination table management data is accepted via the GUI unit 1404 (at a step 1805). Here, the prior-process-policy determination table management data is a set of the prior-process-request level identification code and the prior-process-policy determination table identification code which correspond to the specific-sample prior-process-policy determination table which is the registration target.

Next, the prior-process-policy determination table previous registration unit 1402 accepts the specific-sample prior-process-policy determination table corresponding to the set of the prior-process-request level identification code and the prior-process-policy determination table identification code via the GUI unit 1404 (at a step 1806). Next, the determination table management data and the specific-sample prior-process-policy determination table are attached to the prior-process-policy determination table 114, and are transmitted to the sample-test-device management server 101 (at a step 1807), and this process flow ends.

Alternatively, if the prior-process-policy determination table previous registration unit 1402 judges at the step 1803 that the response is a notification of all determination table registration, a notification indicating that all determination tables have been registered is issued via the GUI unit 1404 (at a step 1808), and this process flow ends.

Figure 9A:
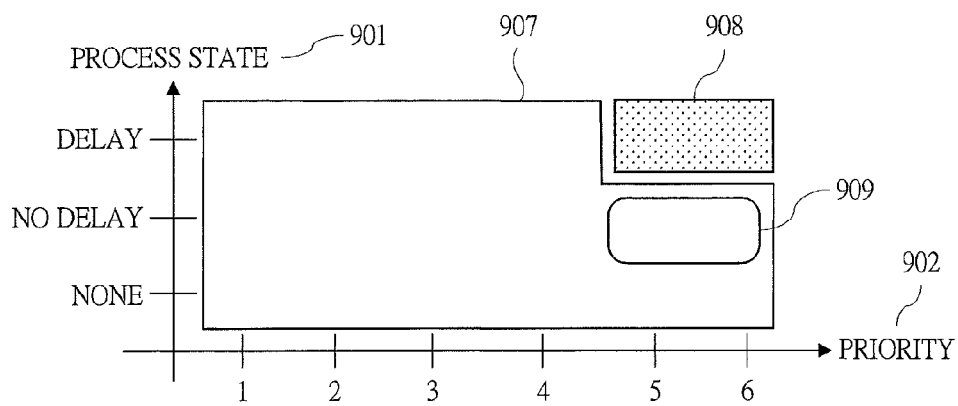
FIGS. 9A to 9C are diagrams each showing a screen image displayed when an operator registers a specific-sample prior-process-policy determination table into a local terminal in the sample test system for performing the sample test method according to the embodiment of the present invention.
Figure 9B:
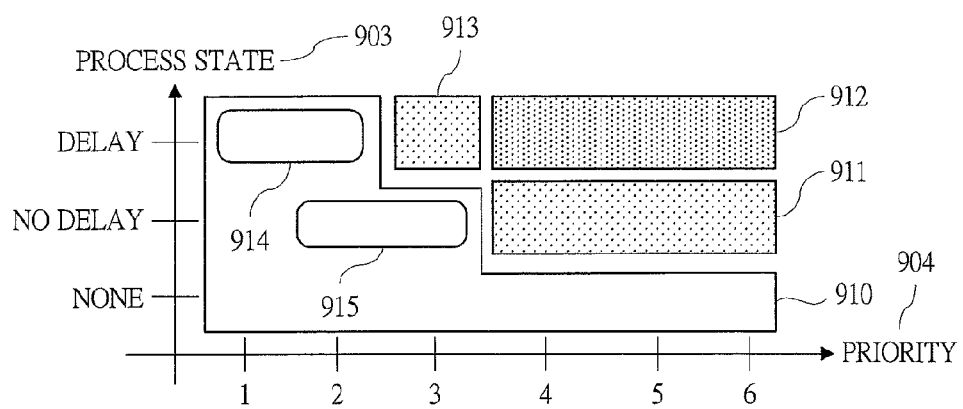
Figure 9C:
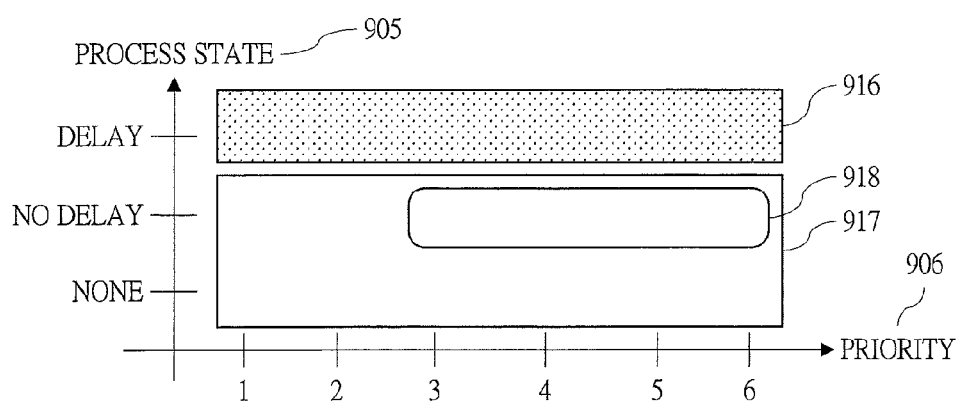

FIGS. 9A to 9C are diagrams each showing a screen image displayed when the operator registers the specific-sample prior-process-policy determination table into the local terminal in the sample test system for performing the sample test method according to the embodiment of the present invention.

In the present embodiment, a specific-sample prior-process-policy determination is registered for the doctor and the other-department server 207. Also, for the doctor, two request levels are assumed, and the specific-sample prior-process-policy determination table is registered for each of them as "as soon as possible" and "soon". Further, for the other-department server, one request level is assumed, and the specific-sample prior-process-policy determination table is registered therefore as "as soon as possible". Based on these assumptions, the operator creates "doctor/as soon as possible" shown in FIG. 9A, "doctor/soon" shown in FIG. 9B, and "other-department server/as soon as possible" shown in FIG. 9C are created.

Respective process states (901, 903, and 905) are process states of sample tests counted for the respective priorities (902, 904, and 906).

In the present embodiment, it is assumed that the process states are counted in three types of "DELAY", "NO DELAY", and "NONE". Each of mediation areas (908, 913, 911, and 916) indicates that the prior process request for the specific sample is to be solved by mediation of the operator. A rejection area 912 indicates that the prior process request for the specific sample is to be solved by rejection.

Each of acceptance areas (907, 910, and 917) indicates that the prior process request for the specific sample is solved by acceptance. Also, each of protection areas (909, 914, 915, and 918) belonging to the respective acceptance areas (907, 910, and 917) indicates that the request is solved by acceptance as the test for the sample to be parallely processed with the prior process request for the specific sample is protected.

Figure 10:
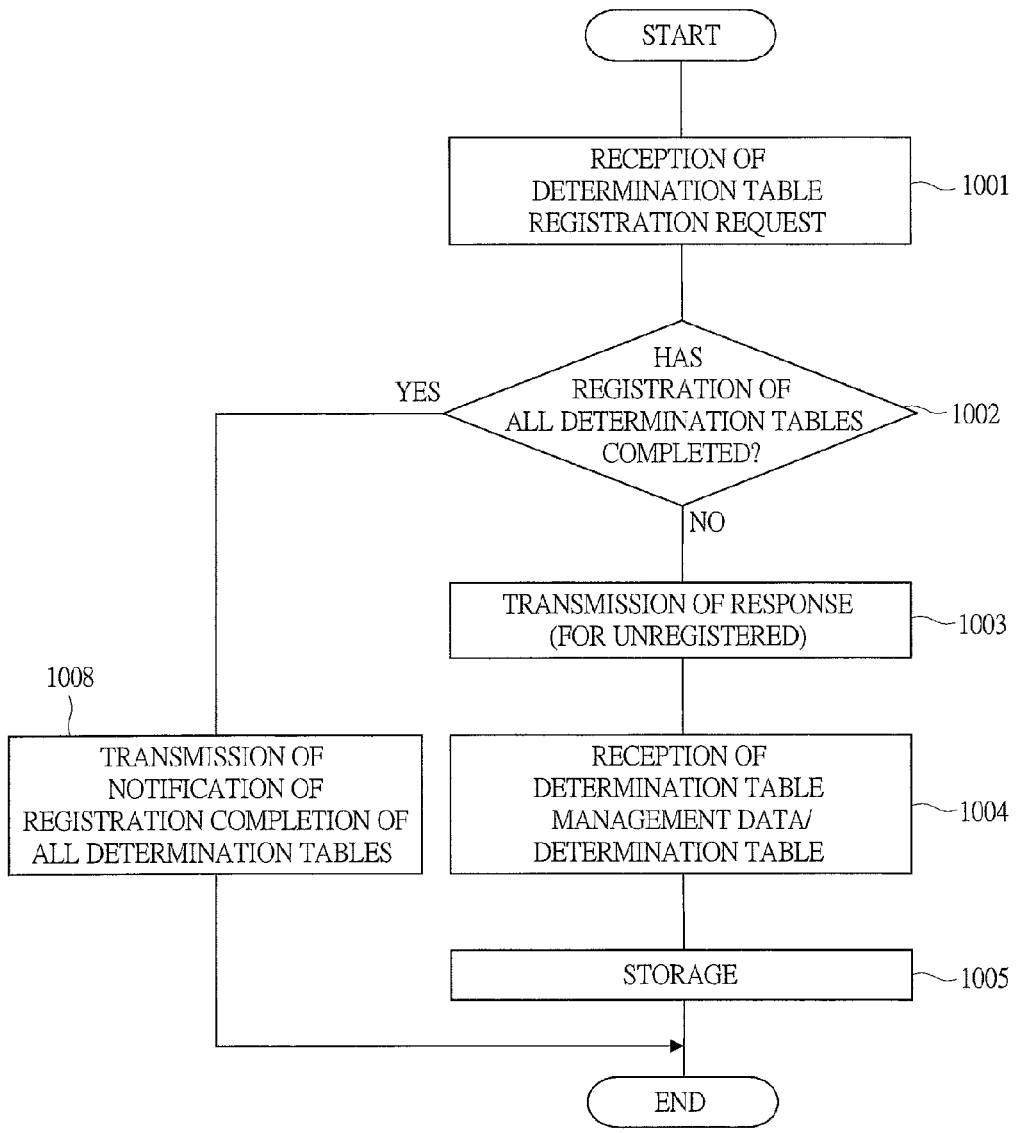
FIG. 10 is a diagram showing a process flow of the sample-test-device management server performed when the operator registers the specific-sample prior-process-policy determination table in the sample test method according to the embodiment of the present invention.

FIG. 10 is a diagram showing a process flow of the sample-test-device management server performed when the operator registers the specific-sample prior-process-policy determination table in the sample test method according to the embodiment of the present invention.

First, the prior-process-policy management unit 501 accepts a registration request of the specific-sample prior-process-policy determination table from the local terminal 107 via the communication unit 505 (at a step 1001).

Next, the prior-process-policy management unit 501 refers to the request-level/determination-table correspondence table 508 of the policy management DB 503, and judges whether all specific-sample prior-process-policy determination tables have been registered or not (at a step 1002).

Next, at the step 1002, if the prior-process-policy management unit 501 judges that all specific-sample prior-process-policy determination tables have not been registered, the prior-process-policy management unit 501 reads the prior-process-request level identification code 802 corresponding to an unregistered specific-sample prior-process-policy determination table from the request-level/determination-table correspondence table 508 of the policy management DB 503, and transmits it to the local terminal 107 via the communication unit 505 (at a step 1003).

Next, the prior-process-policy management unit 501 receives the determination table management data and the specific-sample prior-process-policy determination table from the local terminal 107 (at a step 1004). Next, the prior-process-policy management unit 501 stores the determination table management data and the specific-sample prior-process-policy determination table into the request-level-/determination-table correspondence table 508 and the prior-process-policy determination table storage table 509, respectively (at a step 1005), and the process flow ends.

Alternatively, at the step 1002, if the prior-process-policy management unit 501 judges that all specific-sample prior-process-policy determination tables have been registered, the prior-process-policy management unit 501 transmits a notification indicating that the registration of all specific-sample prior-process-policy determination tables have been completed, to the local terminal 107 (at a step 1008).

Figure 19:
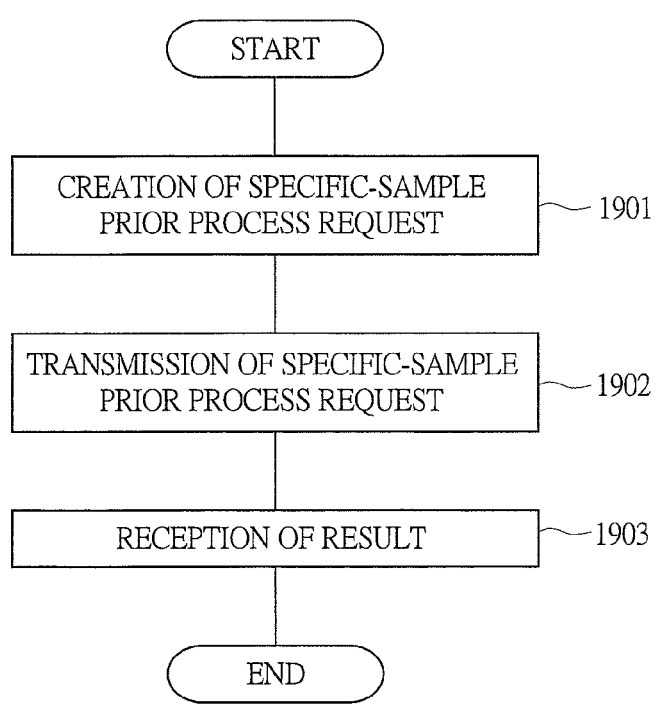
FIG. 19 is a diagram showing a process flow of transmitting a specific-sample prior process request to the sample-test-device management server by the sample access system in the sample test method according to the embodiment of the present invention.

FIG. 19 is a diagram showing a process flow of transmitting the specific-sample prior process request to the sample-test-device management server by the sample access system in the sample test method according to the embodiment of the present invention.

The process flow shown in FIG. 19 is executed by either one or both of the remote terminal 206 and the other-department server 207.

In the present embodiment, a case that the process flow is executed by the remote terminal 206 is described.

First, after the remote terminal 206 acquires the sample registration table stored in the clinical-test-department server 208 via the network 209 and displays the table on the screen, the remote terminal 206 accepts the attribution of the requester and the request level from the doctor, and creates the specific-sample prior process request (at a step 1901).

In the present embodiment, it is assumed that a department of the doctor (for example, a clinic department or others) is specified as the attribution of the requester. However, a name thereof, a name code thereof, or others may be specified.

Next, the remote terminal 206 transmits the specific-sample prior process request 110 to the sample-test-device management server 101 via the network 209, the clinical-test-department server 208, and the network 210 (at a step 1902). Next, the remote terminal 206 receives the result 111 (at a step 1903), displays the result on the screen, and the process flow ends.

Figure 11:
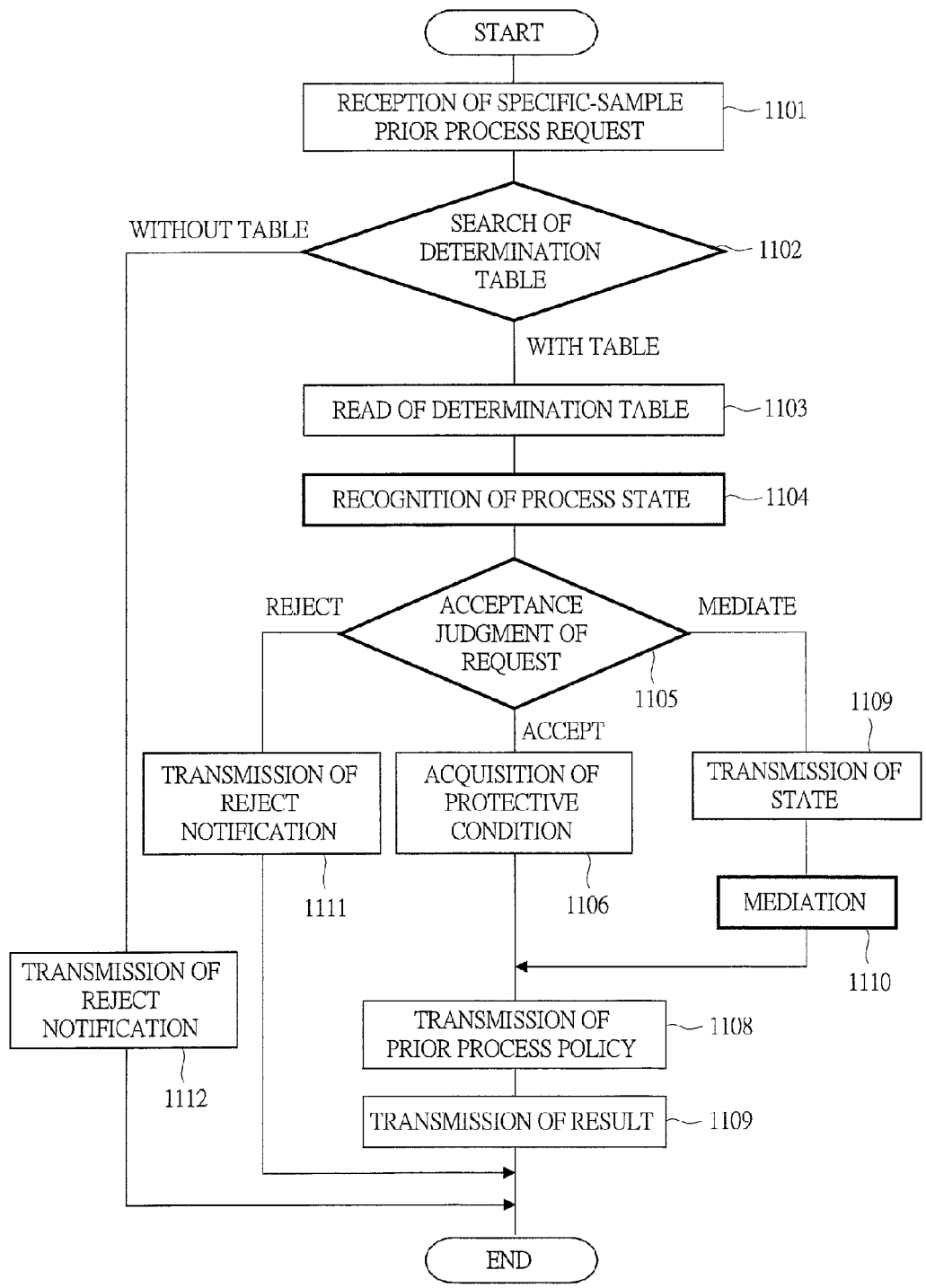
FIG. 11 is a diagram showing a process flow performed when the sample-test-device management server accepts a specific-sample prior process request in the sample test method according to the embodiment of the present invention.

FIG. 11 is a diagram showing a process flow performed when the sample-test-device management server accepts the specific-sample prior process request in the sample test method according to the embodiment of the present invention.

First, the communication unit 505 receives a message via the network 210 and refers to the message identification code attached to the message, so that it recognizes that the message is the specific-sample prior process request 110 and notifies the request management unit 502 of the specific-sample prior process request 110 (at a step 1101).

Next, the request management unit 502 compares the prior-process-request level identification code 1502 attached to the specific-sample prior process request 110 with a content stored in the prior-process-request level identification code 802 of the request-level/determination-table correspondence table 508, so that it judges whether a corresponding specific-sample prior-process-policy determination table is present or not (at a step 1102).

At the step 1102, if the request management unit 502 judges that the corresponding specific-sample prior-process-policy determination table is present, the request management unit 502 reads the specific sample ID 1506 attached to the specific-sample prior process request 110, and notifies the prior-process-policy management unit 501 of the specific sample ID 1506 and the prior-process-policy determination table identification code 801 which is an identification code of the specific-sample prior-process-policy determination table.

The prior-process-policy management unit 501 reads the specific-sample prior-process-policy determination table corresponding to the prior-process-policy determination table identification code 801 from the prior-process-policy determination table storage table 509 (at a step 1103).

Next, the prior-process-policy management unit 501 creates the priority-dependent process state management table 513 by referring to the sample registration table 511 and the sample-dependent process state management table 512, and recognizes the process state of the test (at a step 1104). In the present embodiment, it is assumed that "NONE", "NOT DELAY", or "DELAY" is recognized as the process state for each priority allocated to the sample.

Next, the prior-process-policy management unit 501 executes the acceptance judgment based on the process state and the specific-sample prior-process-policy determination table already selected at the step 1103 (at a step 1105).

If the result of the acceptance judgment is "ACCEPT" at the step 1105, the prior-process-policy management unit 501 acquires the protective condition from the specific-sample prior-process-policy determination table (at a step 1106). In the present embodiment, it is assumed that the priority of the child sample ID 602 corresponding to the specific sample ID 1506 is set as 6 at the step 1106. However, other priorities may be set.

Next, the prior-process-policy management unit 501 searches the corresponding child sample ID 602 from the sample registration table 511 with using the specific sample ID 1506 as a key, and then, creates the prior process policy based on the sample ID, the child sample ID, and the protective condition, and transmits the specific-sample prior process policy 118 to the sample-test-device group 119 via the sample test system management unit 506, the communication unit 507, and the network 211 (at a step 1108).

Next, the prior-process-policy management unit 501 receives the result from the sample-test-device group 119, and transmits the result via the network 210 and the clinical-test-department server 208 (at a step 1109), and the process flow ends.

Alternatively, at the step 1102, if the request management unit 502 judges that the corresponding specific-sample prior-process-policy determination table is not present, the prior-process-policy management unit transmits a rejection notification via the network 210 and the clinical-test-department server 208 (at a step 1112), and the process flow ends.

Alternatively, at the step 1105, if the request acceptance judgment is "REJECT", the prior-process-policy management unit 501 transmits a rejection notification via the network 210 and the clinical-test-department server 208 (at a step 1111), and the process flow ends.

Alternatively, at the step 1105, if the request acceptance judgment is "MEDIATE", the prior-process-policy management unit 501 transmits a mediation notification to the mediation management unit 504. The mediation management unit 504 notifies that the mediation is made by the operator, via the network 210 and the clinical-test-department server 208 (at a step 1109).

Next, the mediation management unit 504 accepts the mediation by the operator, and transmits a mediation completion notification to the prior-process-policy management unit 501 (at a step 1110) to execute a step 1108.

Figure 22:
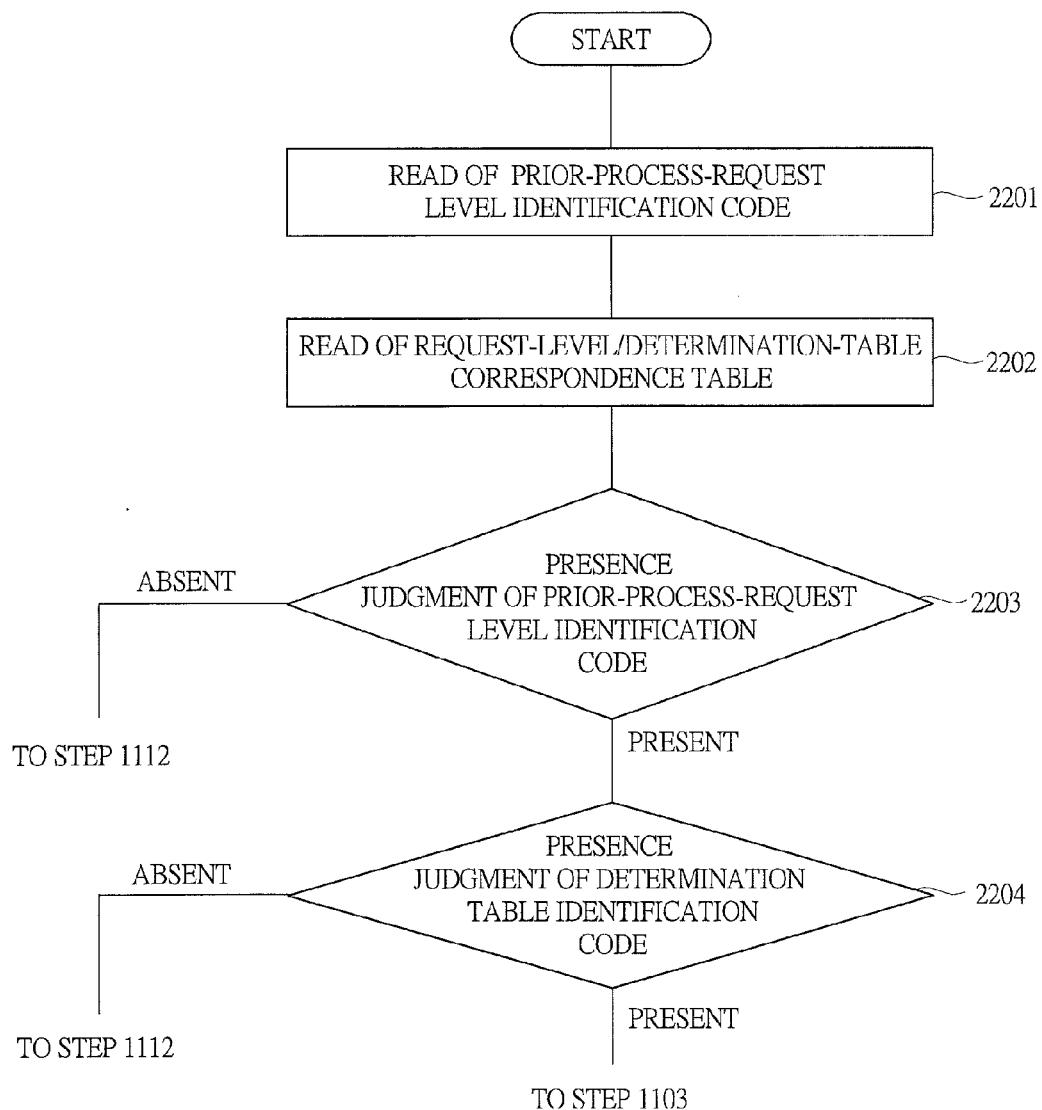
FIG. 22 is a diagram showing a process flow of a request management unit at a step 1102 shown in FIG. 11.

FIG. 22 is a diagram showing a process flow of the request management unit at the step 1102 shown in FIG. 11.

First, the request management unit 502 reads the prior-process-request level identification code 1502 attached to the specific-sample prior process request 110 (at a step 2201).

Next, the request management unit 502 reads the request-level/determination-table correspondence table 508 (at a step 2202). Next, the request management unit 502 judges whether the prior-process-request level identification code 1502 is present or not in the prior-process-request level identification code 802 in the request-level/determination-table correspondence table 508 (at a step 2203).

At the step 2203, if the request management unit 502 judges that the prior-process-request level identification code 1502 is present therein, the request management unit 502 refers to the prior-process-policy determination table identification code 801 to judge whether a code matching the prior-process-request level identification code 1502 is present or not (at a step 2204).

At the step 2204, if the request management unit 502 judges that the matching code is present, the request management unit 502 executes the step 1103. Alternatively, at the step 2204, if the request management unit 502 judges that the matching code is not present, the request management unit 502 executes the step 1112.

At the step 2203, if the request management unit 502 judges that the prior-process-request level identification code 1502 is not present, the request management unit 502 executes the step 1112.

Figure 23:
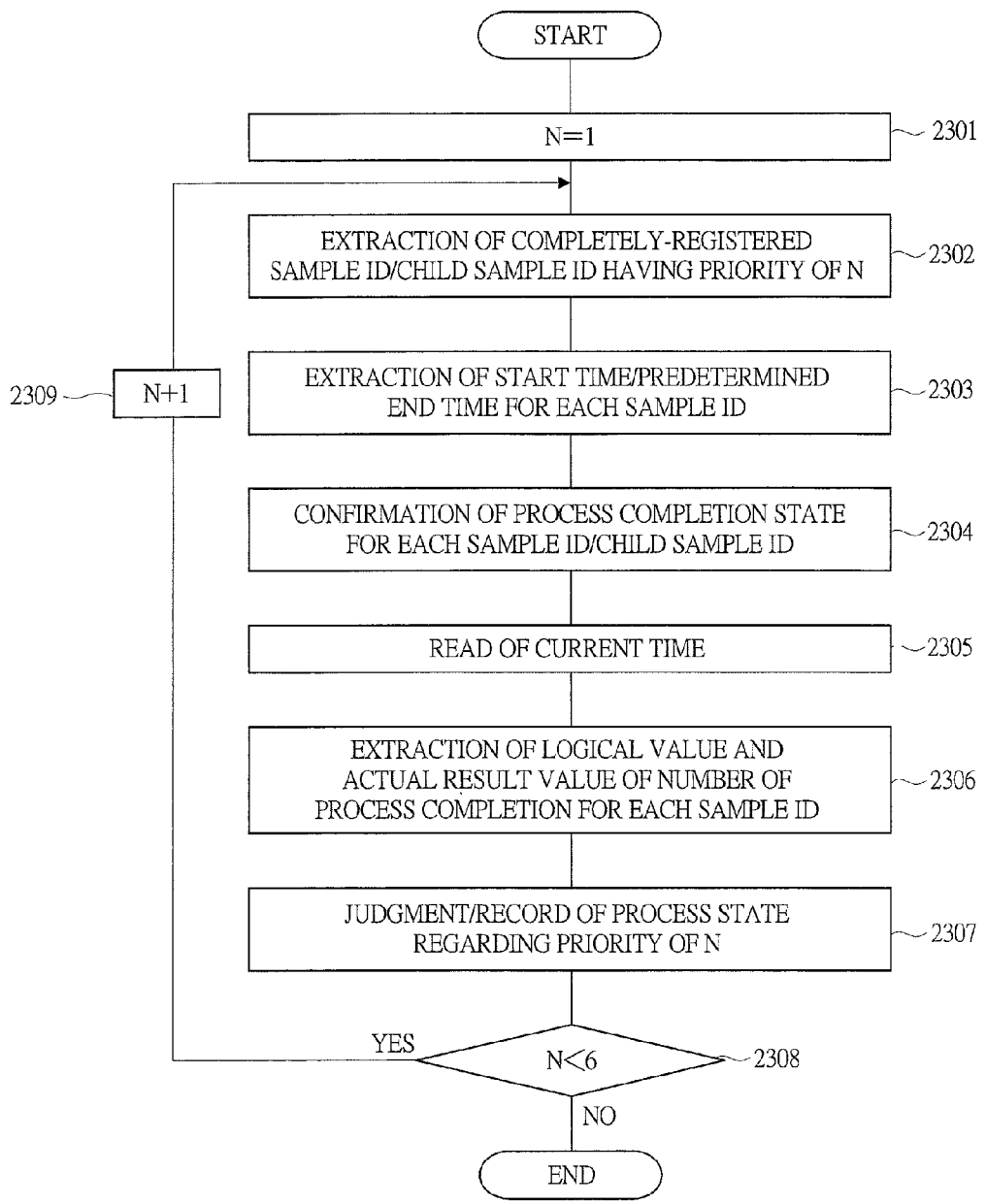
FIG. 23 is a diagram showing a process flow of a prior-process-policy management unit at a step 1104 shown in FIG. 11.

FIG. 23 is a diagram showing a process flow of the prior-process-policy management unit at the step 1104 shown in FIG. 11.

First, the prior-process-policy management unit 501 stores the number of 1 in a loop variable "N" (at a step 2301).

Next, the prior-process-policy management unit 501 extracts the sample ID and the child sample ID registered with a priority of N by referring to the sample ID 601, the child sample ID 602, and the priority 603 in the sample registration table 511 (at a step 2302).

Next, the prior-process-policy management unit 501 extracts the start time and the predetermined end time for each sample ID by referring to the sample ID 601 and the predetermined end time 604 in the sample registration table 511 and the start time in the sample-dependent process state management table 512 (at a step 2303).

Next, the prior-process-policy management unit 501 confirms the process state for each sample ID and child sample ID by referring to the completion flag 608 in the sample-dependent process state management table 512 (at a step 2304).

Next, the prior-process-policy management unit 501 reads the current time from a timer embedded in the sample-test-device management server 101 although not shown in the drawing (at a step 2305). Next, the prior-process-policy management unit 501 calculates a theoretical value and an actual result value of the number of completed processes for each sample ID (at a step 2306). In the present embodiment, it is assumed that the prior-process-policy management unit 501 calculates a ratio between a difference between the start time and the predetermined end time with respect to the elapsed time for each sample ID and calculates the theoretical value based on the ratio. More specifically, it is calculated as "(the number of child sample IDs corresponding to the sample ID)×the elapsed time/(the predetermined end time−the start time)".

Also, in the present embodiment, it is assumed that the prior-process-policy management unit 501 calculates the number of completion flags for each sample ID and calculates the actual result value.

Next, the prior-process-policy management unit 501 compares the theoretical value with the actual result value for each sample ID to judge the process state for the priority of N, and stores the state in a corresponding box in the priority-dependent process state management table 513 (at a step 2307).

Here, in the judgment of the process state for the priority of N, it is assumed that, if the number of sample IDs satisfying "the actual result value>=the theoretical value" occupies a predetermined ratio, "NOT DELAY" is stored in a corresponding box in the priority-dependent process state management table 513.

Alternatively, it is also assumed that, if the number of sample IDs satisfying "the actual result value<the theoretical value" occupies a predetermined ratio, "DELAY" is stored in a corresponding box in the priority-dependent process state management table 513. Further, it is assumed that, if no sample ID belonging to the priority of N is present, "NONE"

is stored in a corresponding box in the priority-dependent process state management table 513.

Next, the prior-process-policy management unit 501 judges whether "N" is smaller than 6 or not (at a step 2308). At the step 2308, if the N is smaller than 6, the prior-process-policy management unit 501 increments the N (at a step 2309), and executes the step 2302. Alternatively, if the N is equal to or larger than 6, the prior-process-policy management unit 501 ends the process flow.

FIG. 24 is a diagram showing a process flow of the prior-process-policy management unit at the step 1105 shown in FIG. 11.

First, the prior-process-policy management unit 501 makes the priority-dependent process state management table 513 correspond to the prior-process-policy determination table already read at the step 1103 shown in FIG. 11 (at a step 2401).

Next, the prior-process-policy management unit 501 judges whether the priority belonging to the rejection request is present or not (at a step 2402). At the step 2402, if it judges that the priority belonging to the rejection request is present, the prior-process-policy management unit 501 executes the step 1111 shown in FIG. 11.

Alternatively, at the step 2402, if it judges that the priority belonging to the rejection request is not present, the prior-process-policy management unit 501 judges whether the priority belonging to the mediation request is present or not (at a step 2403).

At the step 2403, if it judges that the priority belonging to the mediation request is present, the prior-process-policy management unit 501 executes the step 1109 shown in FIG. 11. Alternatively, at the step 2403, if it judges whether the priority belonging to the mediation request is not present, the prior-process-policy management unit 501 executes the step 1106 shown in FIG. 11.

Figure 20:
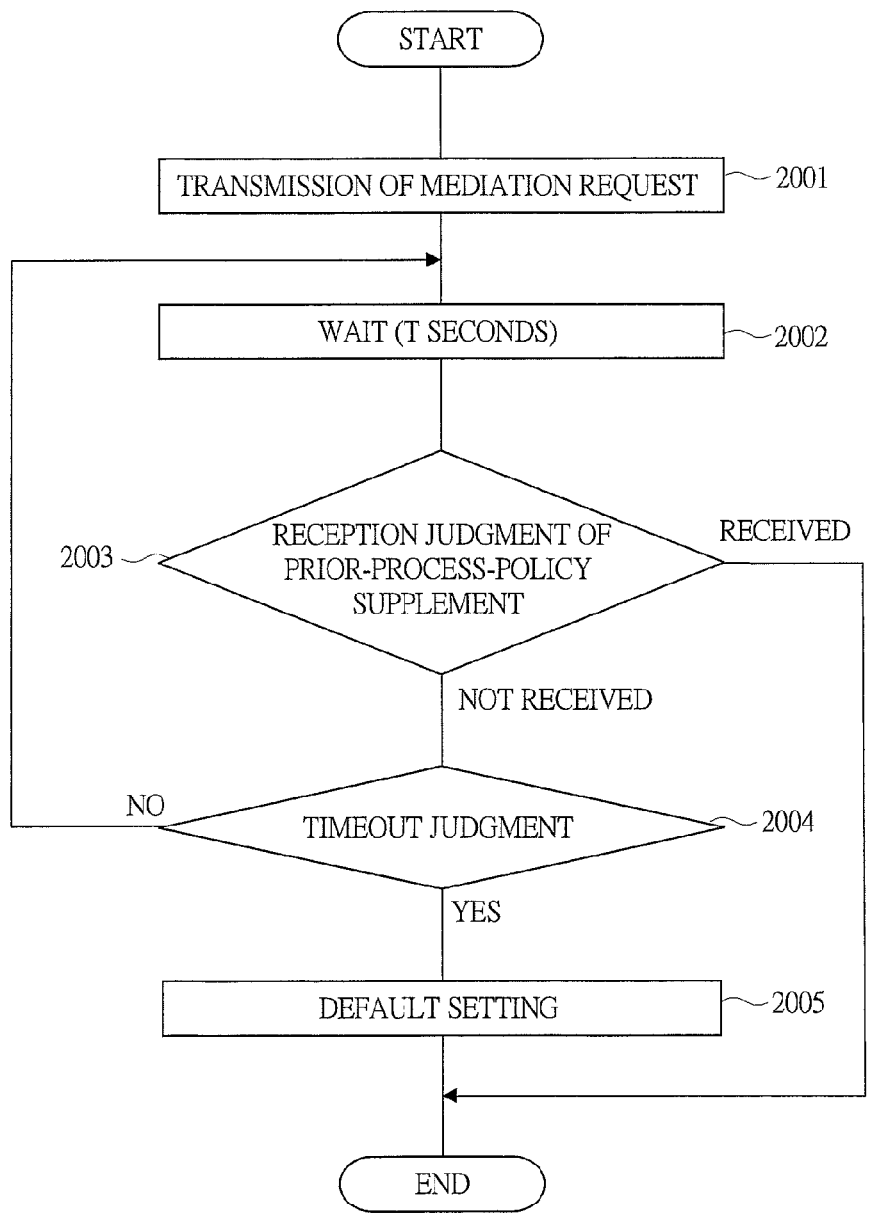
FIG. 20 is a diagram showing a process flow of a mediation management unit at a step 1110 shown in FIG. 11.

FIG. 20 is a diagram showing a process flow of the mediation management unit at the step 1110 shown in FIG. 11.

First, the mediation management unit 504 creates the mediation request based on the specific sample ID, the child sample ID regarding the specific sample, the prior-process-policy determination table, and the process state, and transmits the mediation request to the local terminal 107 (at a step 2001).

Next, the mediation management unit 504 waits for T seconds (at a step 2002). Next, the mediation management unit 504 judges whether the prior-process-policy supplement 116 has been received or not (at a step 2003).

At the step 2003, if it judges that the prior-process-policy supplement 116 has been received, the mediation management unit 504 transmits the specific sample ID 1605, the child sample ID 1606, the protective condition 1607 attached to the prior-process-policy supplement 116 to the prior-process-policy management unit 501, and the process flow ends.

Alternatively, at the step 2003, if it judges that the prior-process-policy supplement 116 has not been received, the mediation management unit 504 judges whether the predetermined time has elapsed or not (at a step 2004).

And, at the step 2004, if it judges that the predetermined time has not elapsed, the process returns to the step 2002.

Alternatively, at the step 2004, if it judges that the predetermined time has elapsed, the mediation management unit sets to change the predetermined protective condition to a default (at a step 2005), and then, transmits the specific sample ID, the child sample ID, and the protective condition to the prior-process-policy management unit 501, and the process flow ends.

Figure 21:
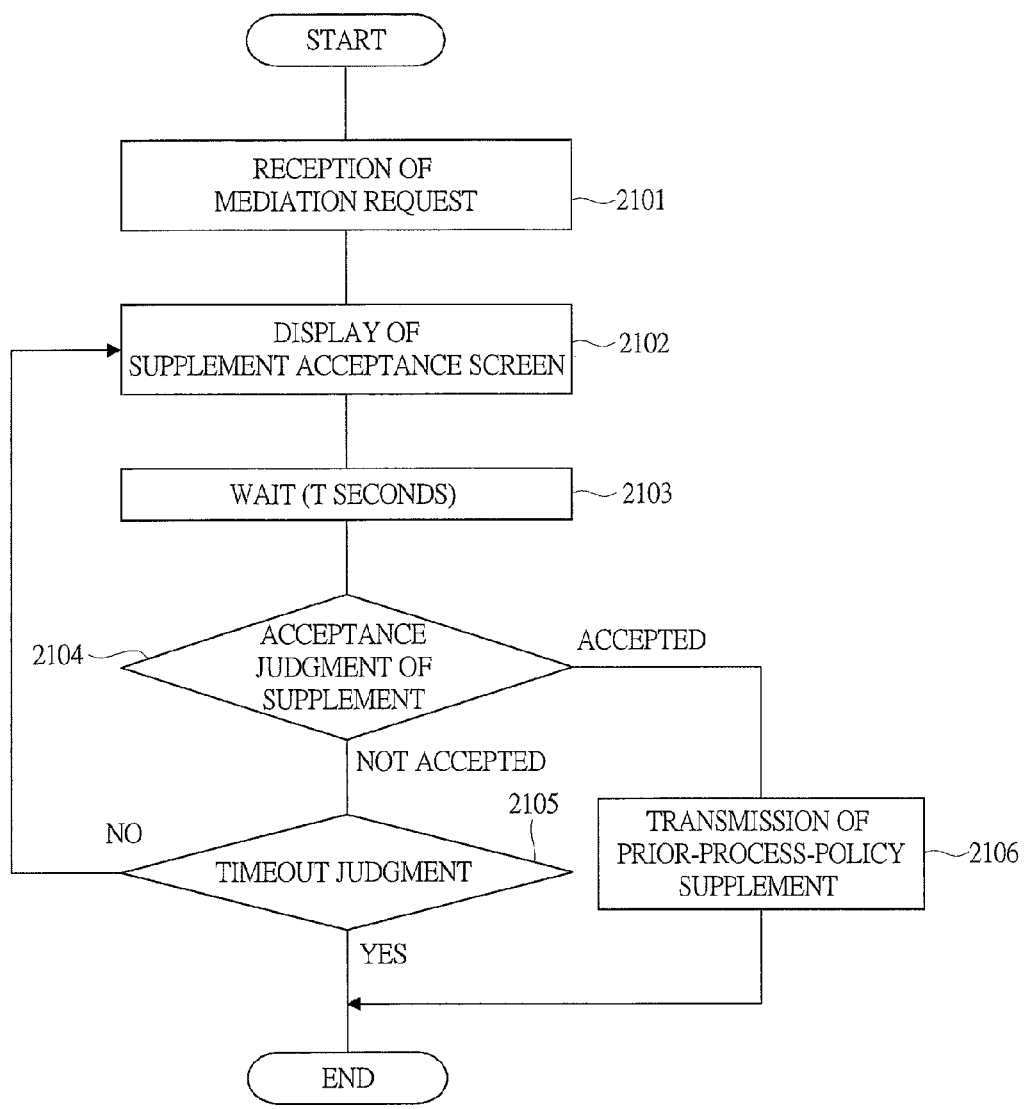
FIG. 21 is a diagram showing a process flow of the local terminal performed when a mediation request is received in the sample test method according to the embodiment of the present invention.

FIG. 21 is a diagram showing a process flow of the local terminal performed when the mediation request is received in the sample test method according to the embodiment of the present invention.

First, the communication unit 1401 refers to the message identification code of the received message. If the code is a code corresponding to the mediation request, it notifies the mediation request unit 1403 of the message attached thereto (at a step 2101).

The mediation request unit 1403 uses the GUI unit 1404 to display the screen for accepting the prior-process-policy supplement (at a step 2102). Next, the mediation request unit 1403 waits for T seconds (at a step 2103).

Next, the mediation request unit 1403 judges whether the prior-process-policy supplement has been received or not (at a step 2104). At the step 2104, if it judges that the prior-process-policy supplement has been received, the mediation request unit 1403 creates the prior-process-policy supplement 116, and transmits the prior-process-policy supplement to the sample-test-device management server 101 (at a step 2106), and the process flow ends.

Alternatively, at the step 2104, if it judges that the prior-process-policy supplement has not been received, the mediation request unit 1403 judges whether the predetermined time has elapsed or not (at a step 2105). At the step 2105, if it judges that the predetermined time has elapsed, the mediation request unit 1403 ends the process flow.

Alternatively, at the step 2105, if it judges that the predetermined time has not elapsed, the mediation request unit 1403 executes the step 2103.

Figure 12:
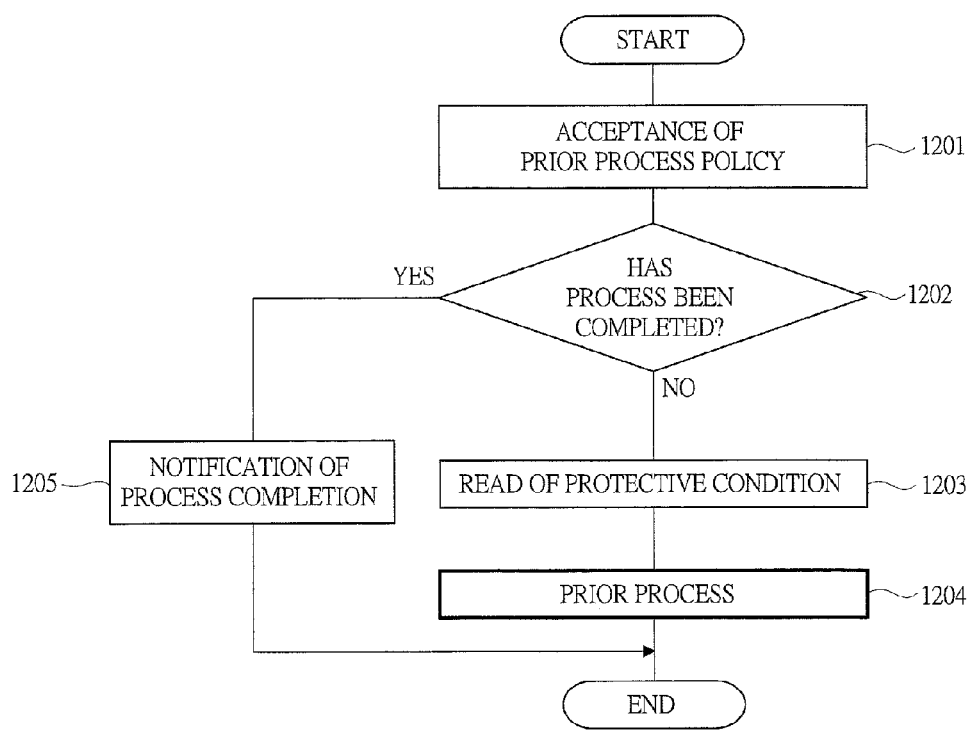
FIG. 12 is a diagram showing a process flow performed when a preprocess device and an analysis device accept a priority process policy in the sample test method according to the embodiment of the present invention.

FIG. 12 is a diagram showing a process flow performed when a preprocess device and an analysis device accept the priority process policy in the sample test method according to the embodiment of the present invention.

Here, an analysis device 202 is exemplified.

First, the communication unit 1307 refers to the message identification code of the received message. If a code indicating the specific-sample prior process policy 118 is confirmed (at a step 1201), it transmits the code to the prior-process-policy acceptance unit 1316.

Next, the prior-process-policy acceptance unit 1316 refers to the specific sample ID 1706 and the child sample ID 1707 attached to the specific-sample prior process policy 118, and the test management memory 1313 to judge whether the sample corresponding to the specific sample ID 1706 and the child sample ID 1707 has been processed or not (at a step 1202).

At the step 1202, if it judges that the sample has been processed, the prior-process-policy acceptance unit 303 notifies the sample-test-device management server 101 of the sample process completion (at a step 1205), and the process flow ends.

Alternatively, at the step 1202, if it judges that the sample has not been processed, the prior-process-policy acceptance unit 1316 reads the protective condition 1708 attached to the specific-sample prior process policy 118 (at a step 1203). Next, it executes the prior process based on the protective condition 1708 and the protective condition group stored in the protective condition storage table 1334 (at a step 1204), and the process flow ends.

Figure 4:
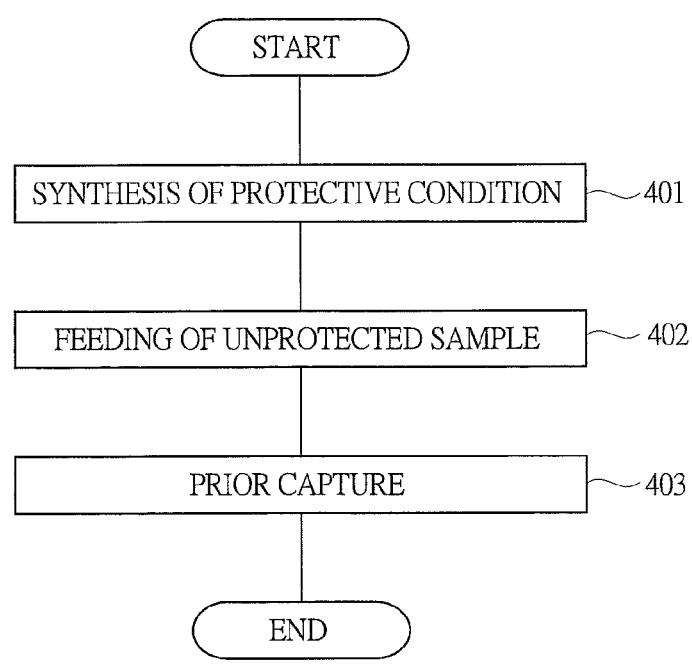
FIG. 4 is a diagram showing a process flow of an analysis device at a step 1204 shown in FIG. 12.

FIG. 4 is a diagram showing a process flow of the analysis device at the step 1204 shown in FIG. 12.

First, the prior-process-policy acceptance unit 1316 reads all protective condition groups stored in the protective condition storage table 1334 and synthesizes the protective condition groups and the protective condition 1708 to create a synthesized protective condition (at a step 401). While it is assumed that the synthesis is made by logical addition (OR) in the present embodiment, the synthesis may be made by logical multiplication (AND) or exclusive OR. After the synthesis, the protective condition 1708 is stored in the protective condition storage table 1334.

Next, the prior-process-policy acceptance unit 1316 transmits the synthesized protective condition to the test control logic unit 1319. The test control logic unit 1319 refers to the synthesized protective condition to extract a priority with a protection flag of 0, and transmits a child sample belonging to the priority from the feeding unit 1328 (at a step 402).

Next, the test control logic unit 1319 draws the child sample from the capturing unit 1331 only when a child sample regarding the specific sample ID is detected (at a step 403).

As described above, in the present embodiment, the sample-test-device management server 101 accepts the prior-process-policy determination table 114 from the local terminal 107, and stores it. When the sample-test-device management server 101 accepts the specific-sample prior process request 110 from the sample access system 108, it selects the specific-sample prior-process-policy determination table based on the prior-process-request level identification code attached to the specific-sample prior process request 110, determines a specific-sample prior process policy based on the prior-process-policy determination table 114 and the process state of the sample test for each priority, and distributes the specific-sample prior process policy to the preprocess device and the analysis device, so that the prior process request for the specific sample is accepted and executed without unnecessarily delaying the process for the sample to which the priority is allocated.

Also, the prior-process-policy determination table 114 can be created in a mode of judging whether the specific-sample prior process request is accepted or not and is mediated or not, and therefore, the policy of the prior process can be defined in a simple mode for the operator.

Further, the sample access system 108 is configured by coupling the local terminal 107 and the other-department server 207 via the network, and the sample-test-device management server 101 accepts the specific-sample prior-process-policy determination table defined for each local terminal 107 and other-department server 207 from the local terminal 107, and therefore, the prior process policy can be determined in accordance with the requester and the request level.

In the foregoing, the invention made by the inventors of the present invention has been concretely described based on the embodiments. However, it is needless to say that the present invention is not limited to the foregoing embodiments and various modifications and alterations can be made within the scope of the present invention.

For example, while the description has been separately made for each of the management units in the sample-test-device management server 101 in the present embodiment, all of them may be configured as one processing unit, and the process of each management unit may be performed by this processing unit.

Also, while the description has been separately made for the sample-test-device group 119 including the preprocess device 201 and the analysis devices 202, 203, and 204 from the sample-test-device management server 101 in the present embodiment, a processing unit having the function of the sample-test-device management server 101 may be provided in the sample-test-device group 119 to configure a sample test system. FIG. 26 shows a configuration example that the sample-test-device management server 101 and the local terminal 107 are embedded in the preprocess device 201. The clinical-test-department server 208, the local terminal 107, the sample-test-device management server 101, and the analysis devices (202, 203, and 204) are coupled with each other via a network 212. Also, they are coupled with the control unit 213 via the sample-test-device management server 101. Even in the configuration shown in FIG. 26, its data structures and process flows can be achieved similarly to the data structures and process flows described in the present embodiment. Also, the local terminal 107 and the sample-test-device management server 101 shown in FIG. 26 may be embedded in the same personal computer such as a work station to be achieved.

INDUSTRIAL APPLICABILITY

The present invention relates to a sample test system used for analyzing a component such as blood (sample), and, more particularly, can be widely applied to a system which utilizes a preprocess device for performing centrifugation, dispensing, or others for the sample prior to the test, an analysis device for analyzing the component of the sample on which the preprocess has been completed, and others.

SYMBOL EXPLANATION

101 . . . sample-test-device management server, 107 . . . local terminal, 108 . . . sample access system, 119 . . . sample-test-device group, 201 . . . preprocess device, 202, 203, and 204 . . . analysis device, 205 . . . transferring path, 206 . . . remote terminal, 207 . . . other-department server, 208 . . . clinical-test-department server, 209 . . . network, 302 . . . communication unit, 303 . . . prior-process-policy acceptance unit, 304 . . . test control logic unit, 305 . . . test progress management unit, 307 . . . control unit, 308, 309, 310, and 311 . . . preprocess unit, 322 . . . protective condition storage table, 306 . . . test management memory, 314, 316, 318, and 320 . . . feeding unit, 315, 317, 319, and 321 . . . capturing unit, 501 . . . prior-process-policy management unit, 502 . . . request management unit, 503 . . . policy management DB, 504 . . . mediation management unit, 505 . . . communication unit, 506 . . . sample-test-system management unit, 507 . . . communication unit, 508 . . . request-level/determination-table correspondence table, 509 . . . prior-process-policy determination table storage table, 510 . . . test management memory, 511 . . . sample registration table, 512 . . . sample-dependent process state management table, 513 . . . priority-dependent process state management table, 1304, 1305, and 1306 . . . control unit, 1307, 1308, and 1309 . . . communication unit, 1310, 1311, and 1312 . . . test progress management unit, 1316, 1317, and 1318 . . . prior-process-policy acceptance unit, 1319, 1320, and 1321 . . . test control logic unit, 1322, 1323, and 1324 . . . network, 1325, 1326, and 1327 . . . analysis unit, 1334, 1335, and 1336 . . . protective condition storage table, 1313, 1314, and 1315 . . . test management memory, 1328, 1329, and 1330 . . . feeding unit, 1331, 1332, and 1333 . . . capturing unit, 1401 . . . communication unit, 1402 . . . prior-process-policy determination table previous registration unit, 1403 . . . mediation request unit, 1404 . . . GUI unit

The invention claimed is:

1. A sample-test-device system comprising:
a sample-test-device group and a sample-test-device management server coupled with the sample test device group via a network, the sample-test-device management server comprising:
  a storage unit which stores sample priority-process-policy information including at least one of a rejection area having rejection information indicating a rejection of a priority process request and an acceptance area having acceptance information indicating an acceptance of the priority process request; and
  a processing unit which:
    determines, when a sample priority process request containing information indicating a sample ID and a priority-process-request level is accepted, a specific sample priority process policy for a sample corresponding to the sample ID based on a process state of the sample and the priority-process-request level by referring to the sample priority-process-policy information and selecting either the rejection or the acceptance of the sample priority process request; and
    if the acceptance is determined for the sample priority process request, the processing unit transmits information indicating the specific-sample priority process policy for the sample to the sample test device group; and
  when the information indicating the specific-sample priority process policy is received, the sample-test-device group:
    judges whether a process regarding the sample ID has been completed or not;
    executes a sample test based on the specific-sample priority process policy only if the process has not been completed; and
    sets the priority corresponding to the specific-sample priority process policy as the priority of the sample.

2. The sample-test-device management server according to claim 1, wherein
  the specific sample priority-process-policy information contains information of a plurality of different priority process policies in accordance with the process state of the sample and the priority-process-request level thereof, which was previously defined in accordance with the inquiry pattern for requesting the priority change.

3. The sample-test-device management server according to claim 1, wherein
  the specific-sample priority-process-policy information is configured of at least one of a rejection area and an acceptance area including a protection area, and
  the processing unit determines the sample priority process policy based on the process state of the sample and the priority-process-request level thereof, which was previously defined in accordance with the inquiry pattern for requesting the priority change, by referring to the specific-sample priority-process-policy information and selecting either rejection or acceptance of the sample priority process request, and, if the acceptance is judged for the sample priority process request, the processing unit creates a protective condition by referring to the protection area, specifies the protective condition, and transmits information indicating the specific-sample priority process policy for the sample to the sample test device.

4. The sample-test-device management server according to claim 1, wherein
  the specific-sample priority-process-policy information is configured of at least one of a rejection area, an acceptance area, and a mediation area, and
  the processing unit determines the sample priority process policy based on the process state of the sample and the specific-priority-process-request level by referring to the specific-sample priority-process-policy information and selecting any one of rejection, acceptance, and mediation of the sample priority process request, and, if the mediation is selected, the processing unit accepts priority-process-policy supplement information after the mediation is selected, and determines the priority process policy for the sample based on the priority-process-policy supplement information.

5. The sample-test-device management server according to claim 4, wherein
  a request of the mediation contains at least one of a sample ID, a child sample ID, sample priority-process-policy information, and a process state data.

6. The sample-test-device management server according to claim 4, wherein
  the priority-process-policy supplement information contains at least one of a sample ID, a child sample ID, and a protective condition.

7. A sample test system for executing a sample test, in which a sample-test-device group including a preprocess device and an analysis device, a local terminal, and a sample access system are coupled with each other via a network, the sample test system comprising:
  a policy management database which previously stores a specific-sample priority-process-policy determination table including at least one of a rejection area having rejection information indicating a rejection of a priority process request and an acceptance area having acceptance information indicating an acceptance of the priority process request; and
  a processing unit provided in the sample-test-device group, which:
    selects, when a specific-sample priority process request containing a specific sample ID and a priority-process-request level identification code is accepted from the sample access system, the specific-sample priority-process-policy determination table based on the priority-process-request level identification code and attached to the specific-sample priority process request;
    determines a specific-sample priority process policy based on the specific-sample priority-process-policy determination table and a process state of the sample;
    specifies a sample ID regarding the specific sample ID;
    selects either the rejection or the acceptance of the sample priority process request; and
    if the acceptance is determined for the sample priority process request,
      transmits the specific-sample priority process policy to the preprocess device and the analysis device;
      when the specific-sample priority process policy is received, judges whether a process regarding the sample ID has been completed or not;
      executes the sample test based on the specific-sample priority process policy only if the process has not been completed; and
      sets the priority corresponding to the priority process policy as the priority of the sample.

8. A sample test method for executing a sample test, in which a sample-test-device group including a preprocess device and an analysis device, a sample-test-device management server, a local terminal, and a sample access system are coupled with each other via a network,
  the sample test method comprising the steps of:
  by the sample-test-device management server including a processing unit, previously storing a specific-sample priority-process-policy determination table including at least one of a rejection area having rejection information indicating a rejection of a priority process request and an acceptance area having acceptance information indicating an acceptance of the priority process request; and when a specific-sample priority process request containing a specific sample ID and a priority-process-request level identification code is accepted from the sample access system, selecting the specific-sample priority-process-policy determination table based on the priority-process-request level identification code attached to the specific-sample priority process request;

determining a specific-sample priority process policy based on the specific-sample priority-process-policy determination table and a process state of the sample;

specifying a sample ID regarding the specific sample ID;

selecting either the rejection or the acceptance of the sample priority process request; and if the acceptance is determined for the sample priority process request, the processing unit, transmitting the specific-sample priority process policy to the sample-test-device group, and by the sample-test-device group, when the specific-sample priority process policy is received, judging whether a process regarding the sample ID has been completed or not; and executing the sample test based on the specific-sample priority process policy only if the process has not been completed and sets the priority corresponding to the priority process policy as the priority of the sample.

* * * * *